(12) United States Patent
Montagnier

(10) Patent No.: US 9,547,029 B1
(45) Date of Patent: *Jan. 17, 2017

(54) SYSTEM AND METHOD FOR THE ANALYSIS OF DNA SEQUENCES

(71) Applicant: Luc Montagnier, New York, NY (US)

(72) Inventor: Luc Montagnier, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/130,484

(22) Filed: Apr. 15, 2016

Related U.S. Application Data

(63) Continuation of application No. 14/706,336, filed on May 7, 2015, now Pat. No. 9,316,610, which is a
(Continued)

(51) Int. Cl.
*C12Q 1/68* (2006.01)
*G01N 27/327* (2006.01)
(Continued)

(52) U.S. Cl.
CPC .............. *G01R 23/20* (2013.01); *C12Q 1/6806* (2013.01); *G01N 27/025* (2013.01); *G01N 27/44704* (2013.01); *G01N 27/44747* (2013.01); *G01N 27/44791* (2013.01); *C12Q 1/6802* (2013.01); *C12Q 1/689* (2013.01); *G01N 27/3275* (2013.01); *G01N 33/48* (2013.01);
(Continued)

(58) Field of Classification Search
CPC ......... C12Q 1/68; C12Q 1/6802; C12Q 1/689; G01N 27/3275; G01N 33/48; G01N 37/005; G01R 23/16; Y10T 436/143333; Y10T 14/25; Y10T 14/25125; Y10T 14/25375; Y10T 14/25625

USPC ........... 436/63, 94, 171, 174, 175, 177, 179; 435/6.1, 29; 324/71.1, 76.12, 76.24, 663, 324/668, 692

See application file for complete search history.

(56) References Cited

U.S. PATENT DOCUMENTS 4,708,818 A    11/1987   Montagnier et al.
4,759,929 A     7/1988   Chermann et al.
(Continued)

FOREIGN PATENT DOCUMENTS

EP    1112748 A2    7/2001
FR    2700628 A1    7/1994
(Continued)

*Primary Examiner* — Maureen Wallenhorst
(74) *Attorney, Agent, or Firm* — Steven M. Hoffberg, Esq.; Ostrolenk Faber LLP

(57) ABSTRACT

Detecting electromagnetic waves derived from bacterial DNA, by extracting and purifying nucleic acids from a sample; diluting the extracted purified nucleic acids in an aqueous solvent; measuring a low frequency electromagnetic emission over time from the diluted extracted purified nucleic acids in an aqueous solvent; performing a signal analysis of the low frequency electromagnetic emission over time; and producing an output, based on the signal analysis, in dependence on the DNA in the sample. The DNA may be extracted from at least one of blood, feces, urine, saliva, tears, seminal fluid, sweat, seminal and vaginal fluids of a patient, or water to determine, e.g., potability. The samples may be frozen. The extracting and purifying may include diluting the sample with an aqueous buffer and mixing; degrading proteins in the diluted sample; precipitating DNA from the buffer solution; and resuspending the precipitated DNA in an aqueous solution.

20 Claims, 46 Drawing Sheets

Related U.S. Application Data continuation of application No. 14/273,679, filed on May 9, 2014, now Pat. No. 9,029,165, which is a continuation of application No. 13/835,162, filed on Mar. 15, 2013, now Pat. No. 8,736,250, which is a continuation of application No. 12/560,772, filed on Sep. 16, 2009, now Pat. No. 8,405,379.

(60) Provisional application No. 61/098,227, filed on Sep. 18, 2008, provisional application No. 61/098,405, filed on Sep. 19, 2008.

(51) Int. Cl.
*G01N 33/48* (2006.01)
*G01N 37/00* (2006.01)
*G01R 23/16* (2006.01)
*G01R 23/20* (2006.01)
*G01N 27/02* (2006.01)
*G01N 27/447* (2006.01)

(52) U.S. Cl.
CPC ............ *G01N 37/005* (2013.01); *G01R 23/16* (2013.01); *Y10T 436/143333* (2015.01)

(56) References Cited

U.S. PATENT DOCUMENTS

| | | |
|---|---|---|
| 4,798,797 A | 1/1989 | Montagnier et al. |
| 4,839,288 A | 6/1989 | Montagnier et al. |
| 5,003,000 A | 3/1991 | Bock et al. |
| 5,030,714 A | 7/1991 | Alizon et al. |
| 5,030,718 A | 7/1991 | Montagnier et al. |
| 5,034,511 A | 7/1991 | Alizon et al. |
| 5,051,496 A | 9/1991 | Alizon et al. |
| 5,055,391 A | 10/1991 | Montagnier et al. |
| 5,066,782 A | 11/1991 | Montagnier et al. |
| 5,079,342 A | 1/1992 | Alizon et al. |
| 5,135,864 A | 8/1992 | Montagnier et al. |
| 5,169,763 A | 12/1992 | Kieny et al. |
| 5,173,400 A | 12/1992 | Montagnier et al. |
| 5,188,963 A | 2/1993 | Stapleton |
| 5,208,321 A | 5/1993 | Hovanessian et al. |
| 5,217,861 A | 6/1993 | Montagnier et al. |
| 5,221,610 A | 6/1993 | Montagnier et al. |
| 5,268,265 A | 12/1993 | Montagnier et al. |
| 5,304,481 A | 4/1994 | Davies et al. |
| 5,306,614 A | 4/1994 | Alizon et al. |
| 5,310,651 A | 5/1994 | Alizon et al. |
| 5,312,902 A | 5/1994 | Montagnier et al. |
| 5,358,937 A | 10/1994 | Huynh Dinh et al. |
| 5,364,933 A | 11/1994 | Montagnier et al. |
| 5,374,519 A | 12/1994 | Montagnier et al. |
| 5,403,918 A | 4/1995 | Metz |
| 5,407,811 A | 4/1995 | Montagnier et al. |
| 5,470,702 A | 11/1995 | Hovanessian et al. |
| 5,514,542 A | 5/1996 | Nowinski et al. |
| 5,545,520 A | 8/1996 | Collandre et al. |
| 5,545,726 A | 8/1996 | Alizon et al. |
| 5,550,052 A | 8/1996 | Montagnier et al. |
| 5,578,715 A | 11/1996 | Alizon et al. |
| 5,580,739 A | 12/1996 | Alizon et al. |
| 5,597,896 A | 1/1997 | Montagnier et al. |
| 5,610,035 A | 3/1997 | Montagnier et al. |
| 5,618,701 A | 4/1997 | Landegren |
| 5,626,617 A | 5/1997 | Brewitt |
| 5,629,286 A | 5/1997 | Brewitt |
| 5,672,689 A | 9/1997 | Kieny et al. |
| 5,677,123 A | 10/1997 | Montagnier et al. |
| 5,688,637 A | 11/1997 | Moncany et al. |
| 5,688,646 A | 11/1997 | Montagnier et al. |
| 5,698,392 A | 12/1997 | Collandre et al. |
| 5,747,242 A | 5/1998 | Alizon et al. |
| 5,770,703 A | 6/1998 | Alizon et al. |
| 5,773,602 A | 6/1998 | Alizon et al. |
| 5,786,177 A | 7/1998 | Moncany et al. |
| 5,795,577 A | 8/1998 | Kieny et al. |
| 5,807,992 A | 9/1998 | Hovanessian et al. |
| 5,824,482 A | 10/1998 | Alizon et al. |
| 5,830,641 A | 11/1998 | Montagnier et al. |
| 5,843,638 A | 12/1998 | Montagnier et al. |
| 5,858,651 A | 1/1999 | Alizon et al. |
| 5,866,319 A | 2/1999 | Alizon et al. |
| 5,869,631 A | 2/1999 | Alizon et al. |
| 5,874,260 A | 2/1999 | Cleuziat et al. |
| 5,889,158 A | 3/1999 | Montagnier et al. |
| 5,976,785 A | 11/1999 | Alizon et al. |
| 6,024,734 A | 2/2000 | Brewitt |
| 6,037,165 A | 3/2000 | Montagnier et al. |
| 6,048,685 A | 4/2000 | Alizon et al. |
| 6,054,565 A | 4/2000 | Alizon et al. |
| 6,056,963 A | 5/2000 | Montagnier et al. |
| 6,142,927 A | 11/2000 | Clark |
| 6,162,439 A | 12/2000 | Alizon et al. |
| 6,194,142 B1 | 2/2001 | Moncany et al. |
| 6,197,496 B1 | 3/2001 | Montagnier et al. |
| 6,232,455 B1 | 5/2001 | Kroeger et al. |
| 6,261,571 B1 | 7/2001 | Hovanessian et al. |
| 6,261,762 B1 | 7/2001 | Alizon et al. |
| 6,265,149 B1 | 7/2001 | Montagnier et al. |
| 6,284,454 B1 | 9/2001 | Alizon et al. |
| 6,296,807 B1 | 10/2001 | Montagnier et al. |
| 6,316,183 B1 | 11/2001 | Alizon et al. |
| 6,322,964 B1 | 11/2001 | Cosand et al. |
| 6,337,179 B1 | 1/2002 | Alizon et al. |
| 6,355,789 B1 | 3/2002 | Alizon et al. |
| 6,395,495 B1 | 5/2002 | Montagnier et al. |
| 6,399,294 B1 | 6/2002 | Charneau et al. |
| 6,426,073 B1 | 7/2002 | Alizon et al. |
| 6,428,952 B1 | 8/2002 | Montagnier et al. |
| 6,429,306 B1 | 8/2002 | Montagnier et al. |
| 6,485,480 B1 | 11/2002 | Brewitt |
| 6,514,691 B1 | 2/2003 | Alizon et al. |
| 6,518,015 B1 | 2/2003 | Alizon et al. |
| 6,541,978 B1 | 4/2003 | Benveniste et al. |
| 6,544,728 B1 | 4/2003 | Alizon et al. |
| 6,600,023 B1 | 7/2003 | Montagnier et al. |
| 6,608,179 B1 | 8/2003 | Hovanessian et al. |
| 6,627,395 B1 | 9/2003 | Montagnier et al. |
| 6,635,752 B2 | 10/2003 | Alizon et al. |
| 6,664,041 B2 | 12/2003 | Montagnier et al. |
| 6,724,188 B2 | 4/2004 | Butters et al. |
| 6,730,304 B2 | 5/2004 | Alizon et al. |
| 6,951,648 B2 | 10/2005 | Alizon et al. |
| 6,952,652 B2 | 10/2005 | Butters |
| 6,979,535 B2 | 12/2005 | Alizon et al. |
| 6,984,721 B2 | 1/2006 | Montagnier et al. |
| 6,995,558 B2 | 2/2006 | Butters et al. |
| 7,022,814 B1 | 4/2006 | Moncany et al. |
| 7,029,679 B2 | 4/2006 | Alizon et al. |
| 7,078,516 B1 | 7/2006 | Moncany et al. |
| 7,081,747 B2 | 7/2006 | Butters et al. |
| 7,115,363 B1 | 10/2006 | Montagnier et al. |
| 7,122,188 B1 | 10/2006 | Montagnier et al. |
| 7,157,225 B2 | 1/2007 | Charneau et al. |
| 7,205,102 B1 | 4/2007 | Montagnier et al. |
| 7,217,508 B1 | 5/2007 | Wain-Hobson et al. |
| 7,218,764 B2 | 5/2007 | Vaisberg et al. |
| 7,232,654 B1 | 6/2007 | Chermann et al. |
| 7,235,353 B2 | 6/2007 | Mattheakis et al. |
| 7,309,589 B2 | 12/2007 | Montagnier et al. |
| 7,323,318 B2 | 1/2008 | Fan et al. |
| 7,341,731 B2 | 3/2008 | Montagnier et al. |
| 7,412,340 B2 | 8/2008 | Butters |
| 7,507,417 B2 | 3/2009 | Montagnier et al. |
| 7,585,619 B1 | 9/2009 | Alizon et al. |
| 7,626,013 B1 | 12/2009 | Alizon et al. |
| 7,759,477 B2 | 7/2010 | Moncany et al. |
| 7,767,800 B2 | 8/2010 | Alizon et al. |
| 7,777,020 B2 | 8/2010 | Moncany et al. |
| 7,817,840 B2 | 10/2010 | Mattheakis et al. |
| 8,236,324 B2 | 8/2012 | Charneau et al. |
| 8,329,396 B1 | 12/2012 | Alizon et al. |

(56) References Cited

U.S. PATENT DOCUMENTS

| | | | |
|---|---|---|---|
| 8,405,379 B1 * | 3/2013 | Montagnier | G01N 37/005 324/76.12 |
| 8,507,196 B1 | 8/2013 | Alizon et al. | |
| 8,736,250 B1 * | 5/2014 | Montagnier | G01N 37/005 324/663 |
| 9,029,165 B1 * | 5/2015 | Montagnier | G01N 37/005 324/663 |
| 9,133,525 B2 | 9/2015 | Montagnier | |
| 9,316,610 B1 * | 4/2016 | Montagnier | G01N 27/3275 |
| 2001/0006641 A1 | 7/2001 | Montagnier et al. | |
| 2002/0022033 A1 | 2/2002 | Alizon et al. | |
| 2002/0051967 A1 | 5/2002 | Montagnier et al. | |
| 2002/0076691 A1 | 6/2002 | Alizon et al. | |
| 2002/0086285 A1 | 7/2002 | Alizon et al. | |
| 2002/0127144 A1 | 9/2002 | Mehta | |
| 2002/0168628 A1 | 11/2002 | Alizon et al. | |
| 2002/0169112 A1 | 11/2002 | Montagnier | |
| 2002/0177128 A1 | 11/2002 | Alizon et al. | |
| 2003/0049604 A1 | 3/2003 | Charneau et al. | |
| 2003/0070604 A1 | 4/2003 | Holzrichter et al. | |
| 2003/0082523 A1 | 5/2003 | Alizon et al. | |
| 2003/0091985 A1 | 5/2003 | Alizon et al. | |
| 2003/0170658 A1 | 9/2003 | Montagnier et al. | |
| 2003/0186219 A1 | 10/2003 | Alizon et al. | |
| 2003/0191061 A1 | 10/2003 | Brewitt | |
| 2003/0224352 A1 | 12/2003 | Alizon et al. | |
| 2003/0235835 A1 | 12/2003 | Alizon et al. | |
| 2004/0010125 A1 | 1/2004 | Hovanessian et al. | |
| 2004/0022781 A1 | 2/2004 | Spytek et al. | |
| 2004/0038937 A1 | 2/2004 | Benveniste et al. | |
| 2004/0111221 A1 | 6/2004 | Beattie et al. | |
| 2005/0037340 A1 | 2/2005 | Moncany et al. | |
| 2005/0158285 A1 | 7/2005 | Giampapa | |
| 2005/0164173 A1 | 7/2005 | Montagnier | |
| 2005/0203578 A1 | 9/2005 | Weiner et al. | |
| 2005/0255129 A1 | 11/2005 | Montagnier | |
| 2006/0035260 A1 | 2/2006 | Moncany et al. | |
| 2006/0057616 A1 | 3/2006 | Montagnier et al. | |
| 2006/0057699 A1 | 3/2006 | Munderloh | |
| 2006/0078998 A1 | 4/2006 | Puskas et al. | |
| 2006/0241392 A1 | 10/2006 | Feinstein et al. | |
| 2007/0172927 A1 | 7/2007 | Montagnier et al. | |
| 2007/0218489 A1 | 9/2007 | Sampath et al. | |
| 2007/0248537 A1 | 10/2007 | Yang et al. | |
| 2008/0039339 A1 | 2/2008 | Hassibi et al. | |
| 2008/0213773 A1 | 9/2008 | Montagnier et al. | |
| 2008/0261197 A1 | 10/2008 | Charneau et al. | |
| 2008/0287856 A1 | 11/2008 | MacDonald et al. | |
| 2009/0035757 A1 | 2/2009 | Owen et al. | |
| 2009/0111159 A1 | 4/2009 | Brolaski et al. | |
| 2009/0226891 A2 | 9/2009 | Nova et al. | |
| 2010/0041011 A1 | 2/2010 | Van Agthoven et al. | |
| 2010/0137474 A1 | 6/2010 | Goh et al. | |
| 2010/0233296 A1 | 9/2010 | Benveniste et al. | |
| 2010/0260677 A1 | 10/2010 | Bhatia et al. | |
| 2010/0323391 A1 | 12/2010 | Montagnier et al. | |
| 2011/0027774 A1 | 2/2011 | Montagnier | |
| 2011/0076710 A1 * | 3/2011 | Montagnier | G01N 37/005 435/29 |
| 2011/0184025 A1 | 7/2011 | Hensel | |
| 2012/0010859 A1 | 1/2012 | Spera | |
| 2012/0024701 A1 | 2/2012 | Montagnier et al. | |
| 2012/0071543 A1 | 3/2012 | Carter et al. | |
| 2012/0185016 A1 | 7/2012 | Weiner et al. | |
| 2012/0245084 A1 | 9/2012 | Carter et al. | |
| 2013/0143205 A1 | 6/2013 | Montagnier | |
| 2013/0196939 A1 | 8/2013 | Montagnier | |
| 2013/0217000 A1 | 8/2013 | Montagnier | |
| 2013/0224788 A1 | 8/2013 | Montagnier et al. | |
| 2015/0132343 A1 | 5/2015 | Montagnier | |
| 2015/0376724 A1 | 12/2015 | Montagnier | |
| 2016/0002620 A1 | 1/2016 | Montagnier | |

FOREIGN PATENT DOCUMENTS

| | | | |
|---|---|---|---|
| FR | 2811591 A1 | | 1/2002 |
| FR | 2894673 | * | 6/2007 |
| FR | 2894673 A1 | | 6/2007 |
| WO | WO9417406 | | 8/1994 |
| WO | WO9954731 | | 10/1999 |
| WO | WO0001412 | | 1/2000 |
| WO | WO0017637 | | 3/2000 |
| WO | WO0017638 | | 3/2000 |
| WO | WO0204067 | | 1/2002 |
| WO | WO0204958 | | 1/2002 |
| WO | WO2005119271 A1 | | 12/2005 |

* cited by examiner

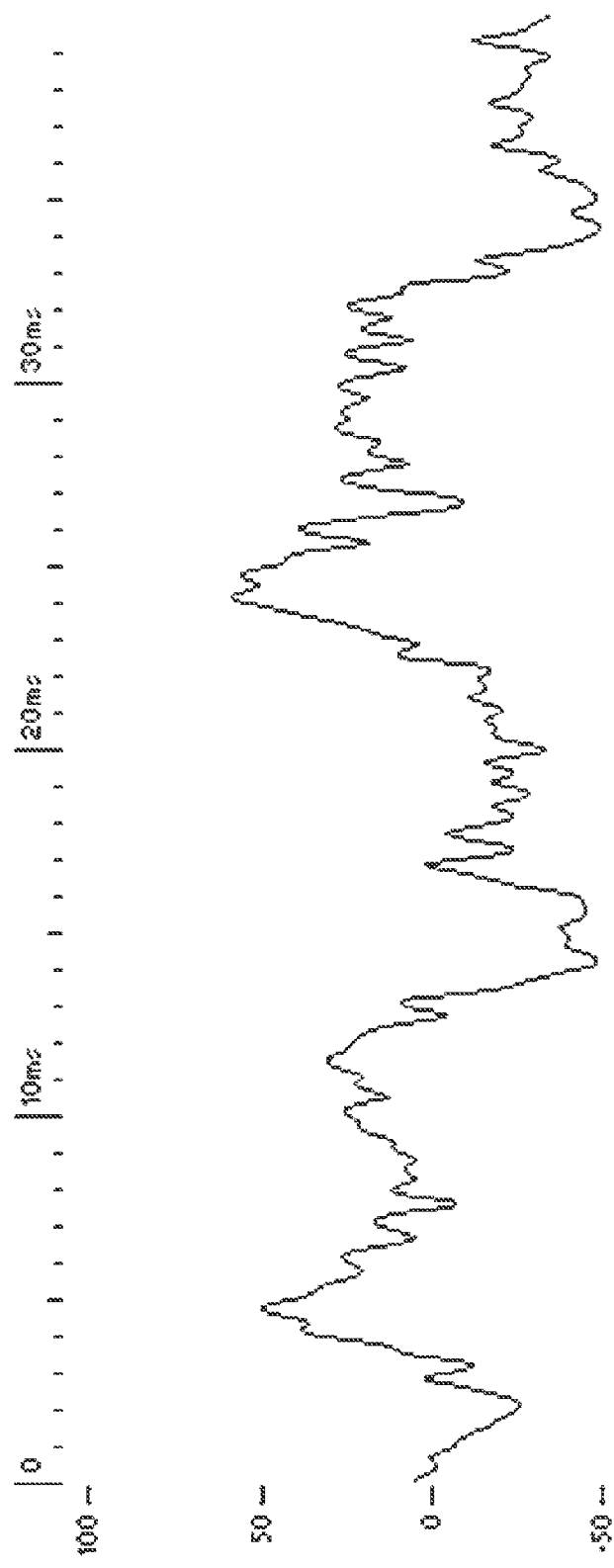

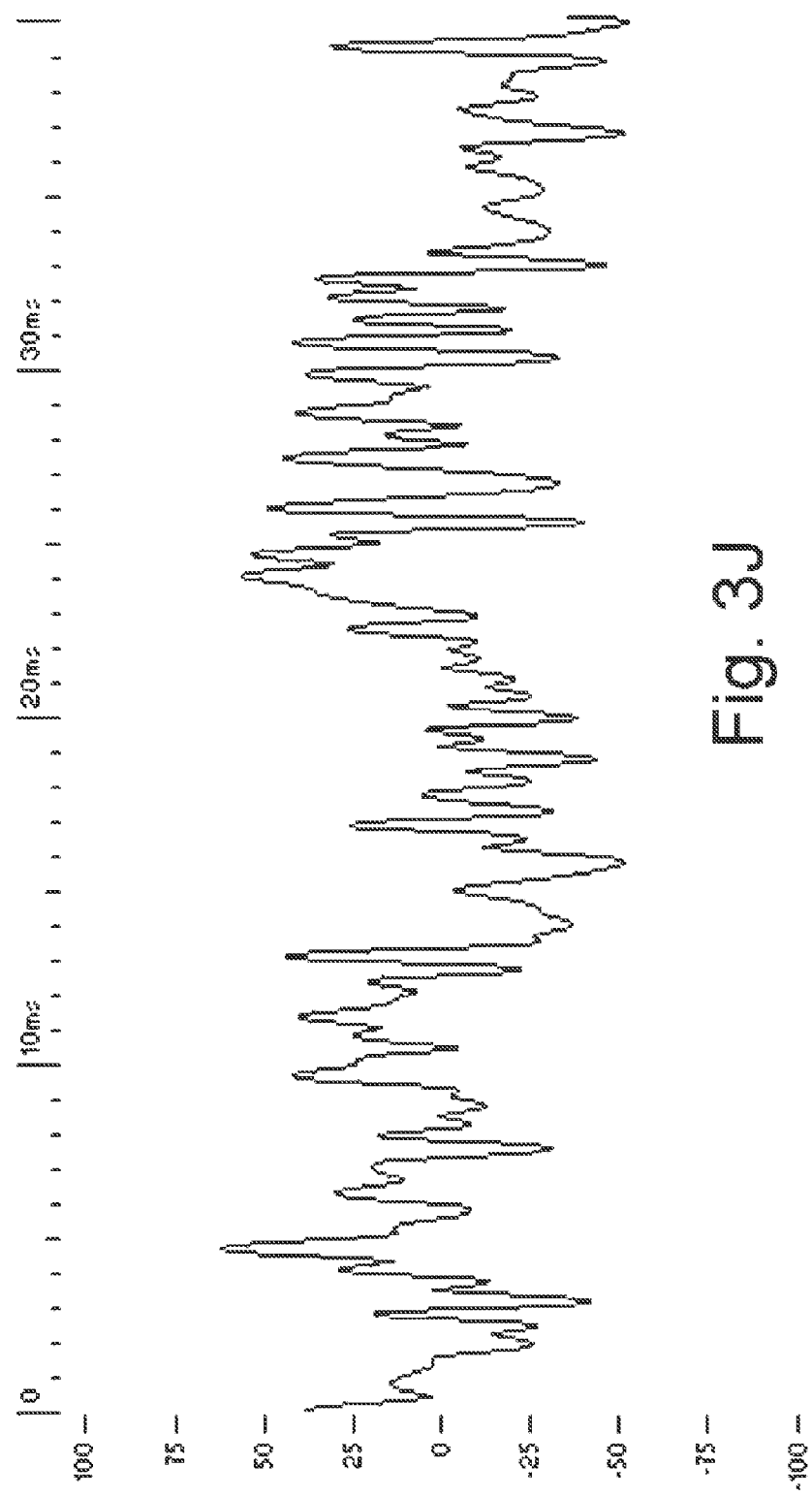

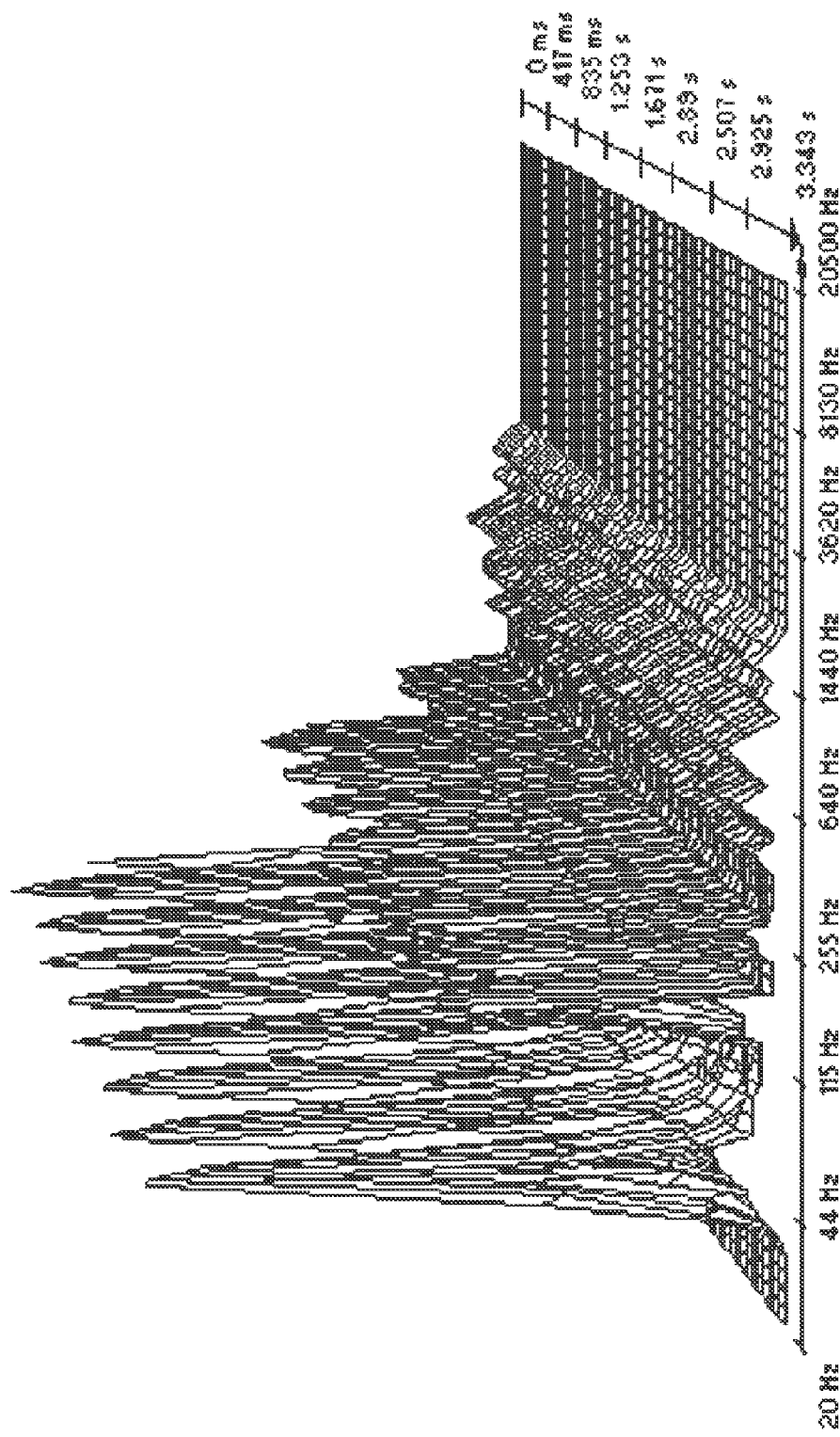

SYSTEM AND METHOD FOR THE ANALYSIS OF DNA SEQUENCES

CROSS REFERENCE TO RELATED APPLICATIONS

The present application is a Continuation of U.S. patent application Ser. No. 14/706,336, filed May 7, 2015, now U.S. Pat. No. 9,316,610, issued Apr. 19, 2016, which is a Continuation of U.S. patent application Ser. No. 14/273,679, filed May 9, 2014, now U.S. Pat. No. 9,029,165, issued May 12, 2015, which is a Continuation of U.S. patent application Ser. No. 13/835,162, filed Mar. 15, 2013, issued May 27, 2014 as U.S. Pat. No. 8,736,250, which is a Continuation of U.S. patent application Ser. No. 12/560,772, filed Sep. 16, 2009, issued Mar. 26, 2013 as U.S. Pat. No. 8,405,379, which claims benefit of priority from U.S. Provisional Patent Application No. 61/098,405, filed Sep. 19, 2008, and U.S. Provisional Patent Application No. 61/098,227, filed Sep. 18, 2008, each of which is expressly incorporated herein by reference in its entirety.

BACKGROUND OF THE INVENTION

In previous patent applications, U.S. patent application Ser. No. 12/097,204 (now abandoned), and PCT/FR2007/001042, filed Jun. 22, 2007, each of which expressly incorporated herein by reference in their entirety, the present applicant has described a new method for detecting some low electromagnetic frequency electromagnetic signals in diluted filtrates of the culture medium of certain bacteria and viruses, as well as in diluted plasma of patients infected by the same agents. The electromagnetic signals (EMS) were believed to be produced by certain defined nanostructures induced by the microorganisms, in high dilutions of in water, the nanostructures being previously removed by filtration.

See (each of which is expressly incorporated herein by reference):

U.S. Pat. No. 6,541,978, WO 00/17638 A (Digibio; Benveniste, Jacques; Guillonnet, Didier) 30 Mar. 2000.
U.S. Ser. No. 09/787,781 (now abandoned), WO 00/17637 A (Digibio; Benveniste, Jacques; Guillonnet, Didier) 30 Mar. 2000.
U.S. Ser. No. 09/720,634 (now abandoned), WO 00/01412 A (Digibio; Benveniste, Jacques; Guillonnet, Didier) 13 Jan. 2000.
FR 2,811,591 A (Digibio) 18 Jan. 2002.
FR 2,700,628 A (Benvenistre Jacques) 22 Jul. 1994.
Benveniste J. et al: "Remote Detection Of Bacteria Using An Electromagnetic/Digital Procedure", Faseb Journal, Fed. Of American Soc. For Experimental Biology, Bethesda, Md., US, No. 5, Part 2, 15 Mar. 1999, page A852, XP008059562 ISSN: 0892-6638.
Thomas et al: "Activation Of Human Neutrophils By Electronically Transmitted Phorbol-Myristate Acetate" Medical Hypotheses, Eden Press, Penrith, US, vol. 54, no. 1, January 2000, pages 33-39, XP008002247, ISSN: 0306-9877.
Benveniste J. et al.: "Qed And Digital Biology" Rivista Di Biologia, Universita Degli Studi, Perugia, IT, vol. 97, no. 1, January 2004, pages 169-172, XP008059428 ISSN: 0035-6050.
Benveniste J. et al.: "A Simple And Fast Method For In Vivo Demonstration Of Electromagnetic Molecular Signaling (Ems) Via High Dilution Or Computer Recording" FASEB Journal, Fed. Of American Soc. For Experimental Biology, Bethesda, Md., US, vol. 13, no. 4, Part 1, 12 Mar. 1999, page A163, Abstr. No. 016209, XP008037356 ISSN: 0892-6638.
Benveniste J: "Biological effects of high dilutions and electromagnetic transmission of molecular signal" [Progress In Neonatology; 25th National Conference Of Neonatology] S. Karger Ag, P.O. Box, Allschwilerstrasse 10, CH-4009 Basel, Switzerland; S. Karger Ag, New York, N.Y., USA Series: Progres En Neonatologie (ISSN 0251-5601), 1995, pages 4-12, XP009070841; and 25ES Journees Nationales De Neonatologie; Paris, France; May 26-27, 1995 ISSN: 3-8055-6208-X.
Benveniste et al.: "Abstract 2392" FASEB Journal, Fed. Of American Soc. For Experimental Biology, Bethesda, Md., US, 22 Apr. 1998, page A412, XP009070843 ISSN: 0892-6638.
Benveniste et al.: "Abstract 2304" FASEB Journal, Fed. Of American Soc. For Experimental Biology, Bethesda, Md., US, 28 Apr. 1994, page A398, XP009070844 ISSN: 0892-6638.

See also, U.S. Pat. Nos. 7,412,340, 7,081,747, 6,995,558, and 6,952,652, each of which is expressly incorporated herein by reference.

SUMMARY OF THE INVENTION

The present invention concerns the identification of the molecules present in, for example, bacteria which are the sources of the signals. In particular, some particular forms and sequences of DNA from potentially pathogenic bacteria may give rise to these signals. The extraction of DNA has the advantage of facilitating the detection of electromagnetic signals from complex biological fluids, even when they have been kept frozen at low temperature. The method is particularly appropriate for the detection, identification and treatment of chronic bacterial infections in diseases associated with autoimmune components, such as rheumatoid arthritis and multiple sclerosis, or in neuropathies of unknown origin such as Alzheimer's and Parkinson's diseases.

In preliminary experiments, the inventor had observed that a pretreatment of a suspension of *Escherichia coli* (*E. Coli*) by 1% formaldehyde did not alter its capacity to induce the electromagnetic signals, while killing the bacteria. This treatment alters the surface proteins of the bacterial cells without attacking their genetic material, i.e., double-helical DNA. This suggested that the source of the signals may be the DNA itself. Indeed, DNA extracted from the bacterial suspension by the classical phenol:chloroform extraction technique was able, upon filtration and appropriate dilutions in water, to emit electromagnetic signals similar to those produced by intact bacteria under the same conditions. DNAse treatment of the extracted DNA solution abolishes the capacity to emit signals, provided one eliminates the source of signal coming from the nanostructures previously induced by the DNA.

It is therefore an object of the invention to provide a method for detecting electromagnetic waves derived from bacterial DNA, comprising extracting and purifying nucleic acids from a sample; diluting the extracted purified nucleic acids in an aqueous solvent; measuring a low frequency electromagnetic emission over time from the diluted extracted purified nucleic acids in an aqueous solvent; performing a signal analysis of the low frequency electromagnetic emission over time; and producing an output, based on the signal analysis, in dependence on the DNA in the sample. The output may vary in dependence on DNA in the sample derived from pathogenic bacteria in plasma of patients suffering from chronic diseases. The sample may contain DNA extracted from at least one of blood or blood plasma, feces, urine, saliva, tears, seminal fluid, sweat, seminal and vaginal fluids of a patient. The sample may also contain DNA extracted from potable water. For example, the sample may contain DNA which is extracted from samples previously frozen and stored at temperatures between about −20° C. and −70° C. The diluting step may, for example, dilute the DNA by about $10^{-7}$ to $10^{-13}$.

The extracting and purifying process may comprise: diluting the sample with an aqueous buffer and mixing; degrading proteins in the diluted sample; precipitating DNA from the buffer solution; and resuspending the precipitated DNA in an aqueous solution. Further, the resuspended DNA may be filtered through at least one submicron filter, wherein the sample measured comprises the filtrate. The filtrate may be diluted in an aqueous solution prior to measuring. The resuspended DNA may be diluted by $10^2$ to $10^{20}$ prior to measurement.

The measuring may comprise placing the diluted extracted purified nucleic acids near an antenna adapted to receive electromagnetic signals having a frequency approaching about 0 Hz and up to 20 kHz, and receiving the electromagnetic signals from the antenna.

The signal analysis may comprise performing a time domain to frequency domain transformation on the signal. Transformed signals from two different samples may be compared. For example, the transform may be a frequency domain (such as an FFT or DFT, generally using an appropriate window function), wavelet domain, or other reversible or irreversible transform. The signal analysis may comprise applying a threshold function to the frequency domain transformed signal. The threshold function may be a static or dynamic or adaptive threshold, and may be uniform or changing over a spectrum of characteristics. The signal analysis may comprise a three-dimensional histogram. The signal analysis may comprise reducing a background noise component of the signal. The signal analysis may comprise selective analysis of signal components having frequencies between about 500-3000 Hz.

The signal analysis may be performed on a general purpose computer, for example having a processor, memory for storing program instructions and data, an operating system, application software, and inputs and outputs, and the output may be presented through a graphic user interface.

BRIEF DESCRIPTION OF THE DRAWINGS

FIGS. 2A, 2B, 2C, 2D, 2E, 2F, 2L, 2M, 2N, and 2O are control samples, showing a noise pattern.

DETAILED DESCRIPTION OF THE INVENTION

Figure 1:
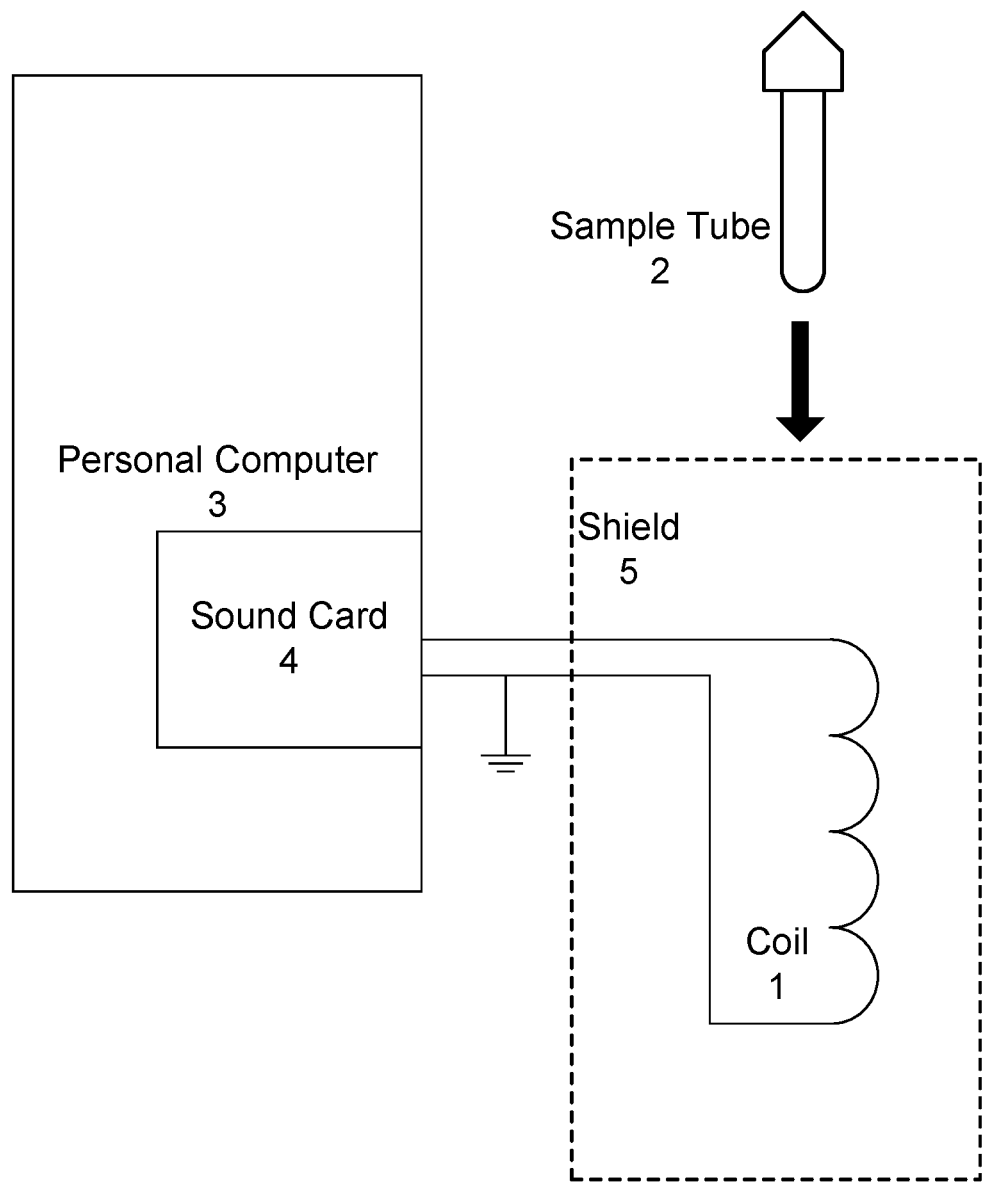
FIG. 1 shows a schematic diagram of the apparatus for recording electromagnetic signals.

A typical experiment is described as follows: First, extreme precautions have to be taken at all steps of the process in order to avoid adventitious contamination from external sources: all manipulations have to be done in a class 100 or better laminar flow hood, and centrifugations are operated in stoppered sterile tubes. The water used for dilutions of reagents and samples has been obtained by distillation at 500° C. (pyrolysis) to destroy any macromolecular organic compound.

1) DNA Extraction:

The sample is first equilibrated at room temperature (15-20° C.), then it is diluted 1:100 in a volume of 400 µl final in sterile PBS 1× in a 2 ml microcentrifuge tube, and mixed by pulse-vortexing for 10 sec.

40 µl of a 10 mg/ml solution of Proteinase K are added (1 mg/ml final concentration) and then 20 µl of an aqueous solution of SDS 10% (Sodium Dodecyl Sulfate) are added (0.5% final concentration). The mixture is mixed by pulse-vortexing for 10 sec, and incubated 15 min at 56° C.

500 µl of Phenol:Chloroform:IsoAmyl Alcohol (25:24:1), are then added and mixed by pulse-vortexing for 20 sec. The mixture is centrifuged for 10 min at room temperature at 6000×9 (8000 rpm). The upper aqueous phase is collected (approximately 500 µl) and placed in a new 2 ml microcentrifuge tube. Cold ethanol, 2.5 volumes (1,125 µl) and 2.5M Sodium Acetate (pH 5.2), 1:10 of final volume (160 µl) are added to precipitate the DNA, mixed by inverting the tube carefully (5-10 times) and left for 15 min at 20° C. The sample is centrifuged for 30 min at 14,000 rpm at 4° C. and the supernatant is discarded. The pellet is washed twice by 500 µl of cold ethanol 70% and the suspension is centrifuged for 10 min at 14,000 rpm at 4° C. The supernatant is discarded and the pellet is dried at room temperature for 15 min. The pellet is then re-suspended in 60 µl Tris 10 mM (pH 7.6), mixed by pipetting and stored at 4° C. for immediate use in the SEM protocol or frozen at −20° C. or preferentially at −70° C. for further analysis.

2) EMS Measurement:

An aliquot of the DNA solution is diluted 1:100 vol/vol in water and the dilution is filtered first through a Millipore filter of pore size 0.45 µm (Millex). The filtrate is filtered again through a 0.1 µm Millipore filter. This filtration step is important, and it has been observed that no signals are detected in its absence at any dilution. In contrast to the microorganism suspensions where the filtration was supposed to retain the bacteria or viruses, this filtration let the DNA pass through, and the latter is therefore still present in the filtrate.

By definition, the "filtrate" is the liquid which has passed through the pores of the filter and is not retained by the filter.

The role of filtration for the DNA solution is probably to dissociate the network of nanostructures which are trapped in a gel at high concentration, thus allowing them to vibrate in resonance with the excitation produced by the electromagnetic background.

The filtration step must be immediately followed by the dilution steps 10 by 10 in water as previously described, for the filtrates of plasma or of microorganism suspensions.

For each dilution, 0.1 ml of the previous dilution is added to 0.9 ml of water in an Eppendorf conical tube, and strongly agitated for 15 seconds in a vortex mixer. Again, 0.1 ml of this solution is diluted in 0.9 ml of water, etc.

Usually, the range of dilutions is made between $10^{-2}$ and $10^{-15}$, eventually $10^{-20}$. Capture and analysis of the EMS is proceeded as previously described in U.S. patent application Ser. No. 12/097,204, and as shown in FIG. 1. Briefly, this method is as follows:

The detection of signals is performed with equipment shown in a schematic view in FIG. 1. The equipment includes a reading solenoid coil (1) with high sensitivity between about 0 and 20,000 Hertz, positioned on a table made of an isolating material, e.g., shield (5). The solutions to be read are distributed in plastic Eppendorf® conical tubes (2), 1.5 milliliter in capacity. The liquid volume is, for example, 1 milliliter, though lesser amounts may be employed. Each sample is read for 6 seconds, twice in a row, and each reading is entered separately. The electric signals delivered by the solenoid (coil 1 of wire surrounding the sample tube 2) are amplified using a sound card (4) input to a personal computer (3) the appropriate software of which may provide a visual representation of the recorded elements.

An amplitude raw global representation is presented. Some background noise is generally present, which can then be filtered. A positive signal is detected when the amplitude exceeds at least 1.5 times the background noise. In general, the detected amplitude is twice and sometimes three times, the background noise. This detected signal is called an SEM electromagnetic signal.

A 3D histogram analysis may be performed, respectively of the background noise and the signal in presence of the sample. The recorded signal may be broken down into individual frequencies through a Fourier transform of the background noise and the signal respectively in the presence of the sample. Of course, other types of signal analysis may be employed, for example wavelet analysis, principal component analysis, or other linear, non-linear, statistical, discrete, etc. analysis techniques which analyze a signal amplitude with respect to time signals, particularly those which extract or emphasize information represented therein.

Figure 4A:
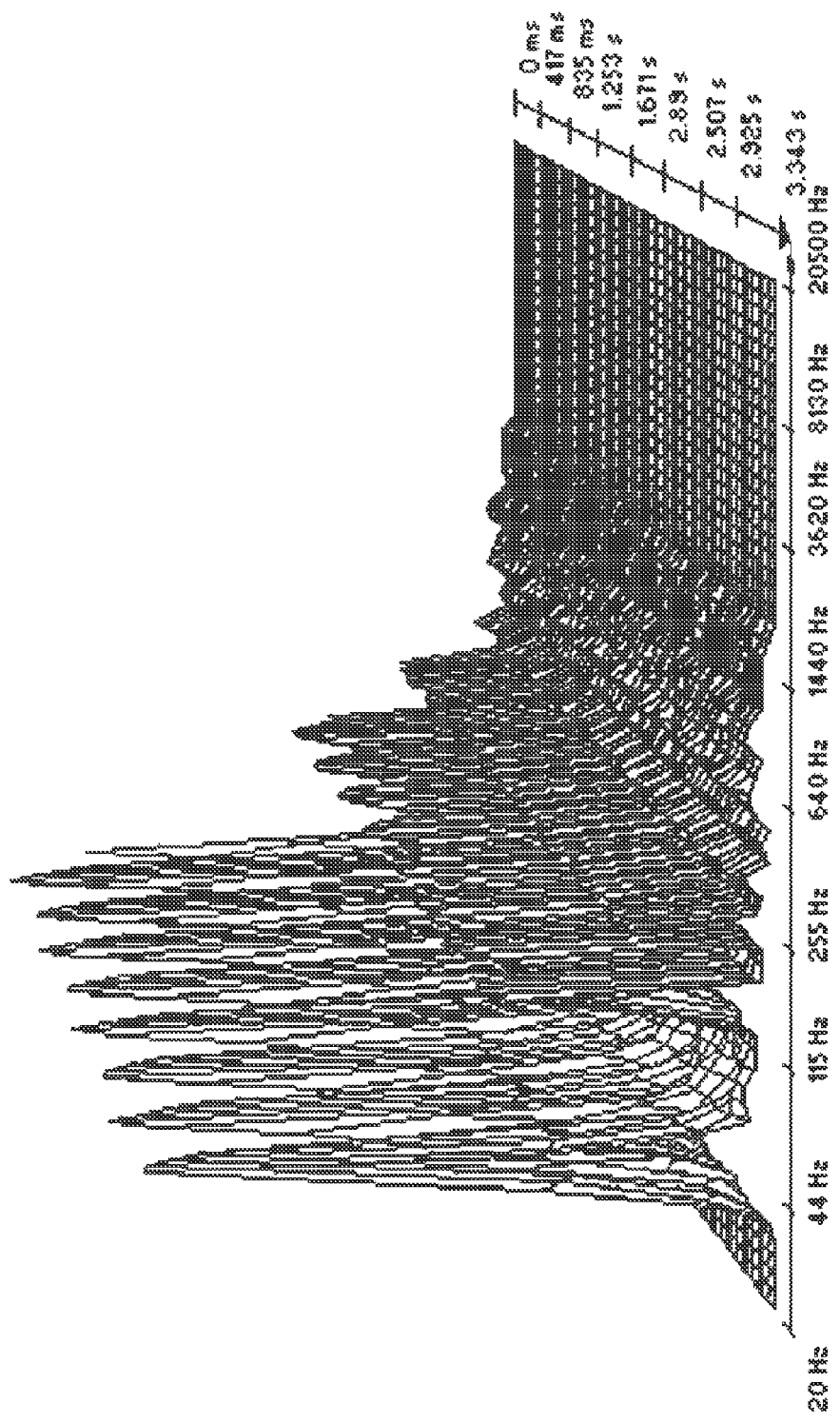
FIGS. 4A-4O show, respectively, a tridimensional Fourier transform as output from Matlab software of the recording, in which the Abscissa shows a range of frequencies from 20 to 20,000 Hz, the ordinate represents the intensity of the waves, and the third dimension represents recordings at different times.
Figure 4B:
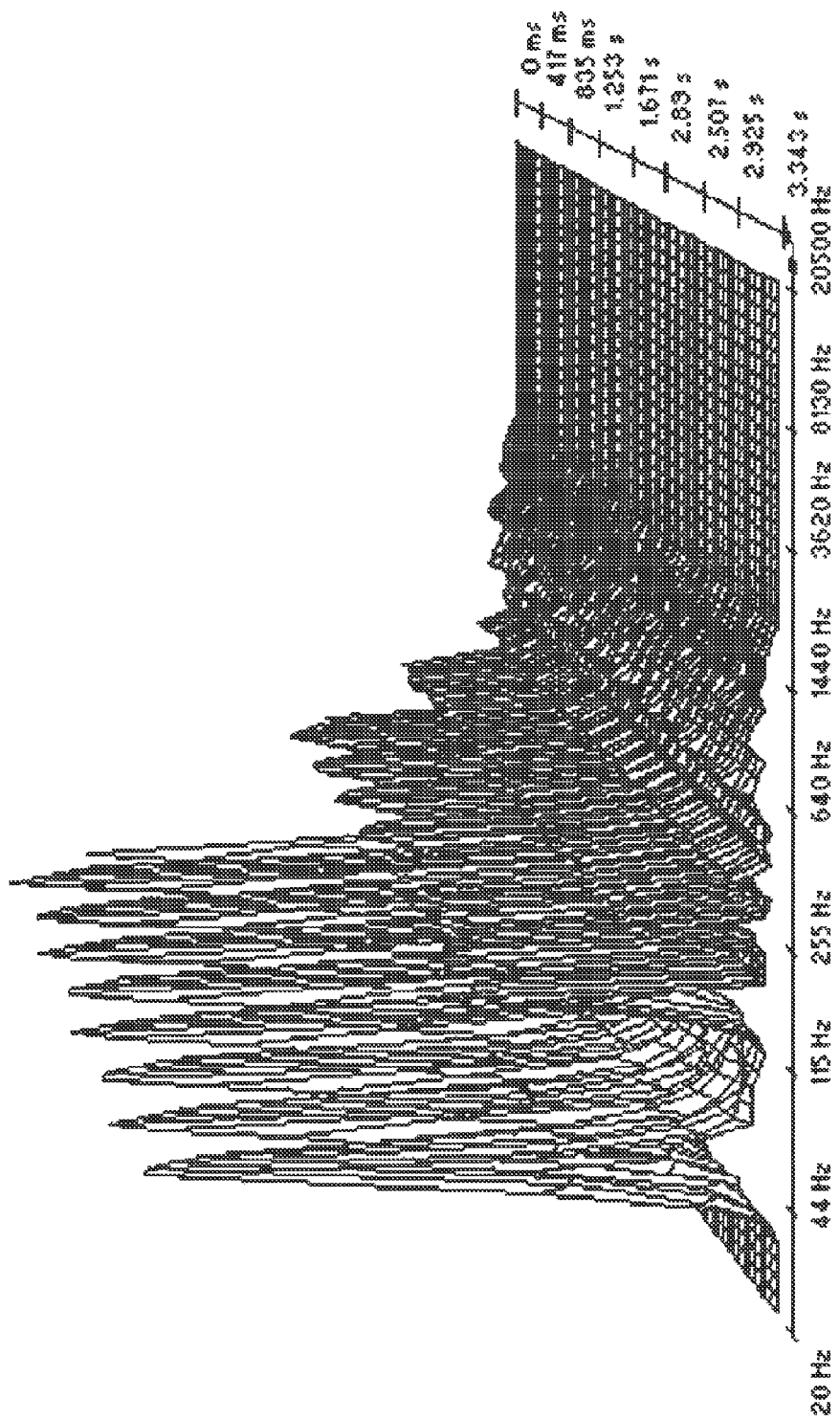
Figure 4C:
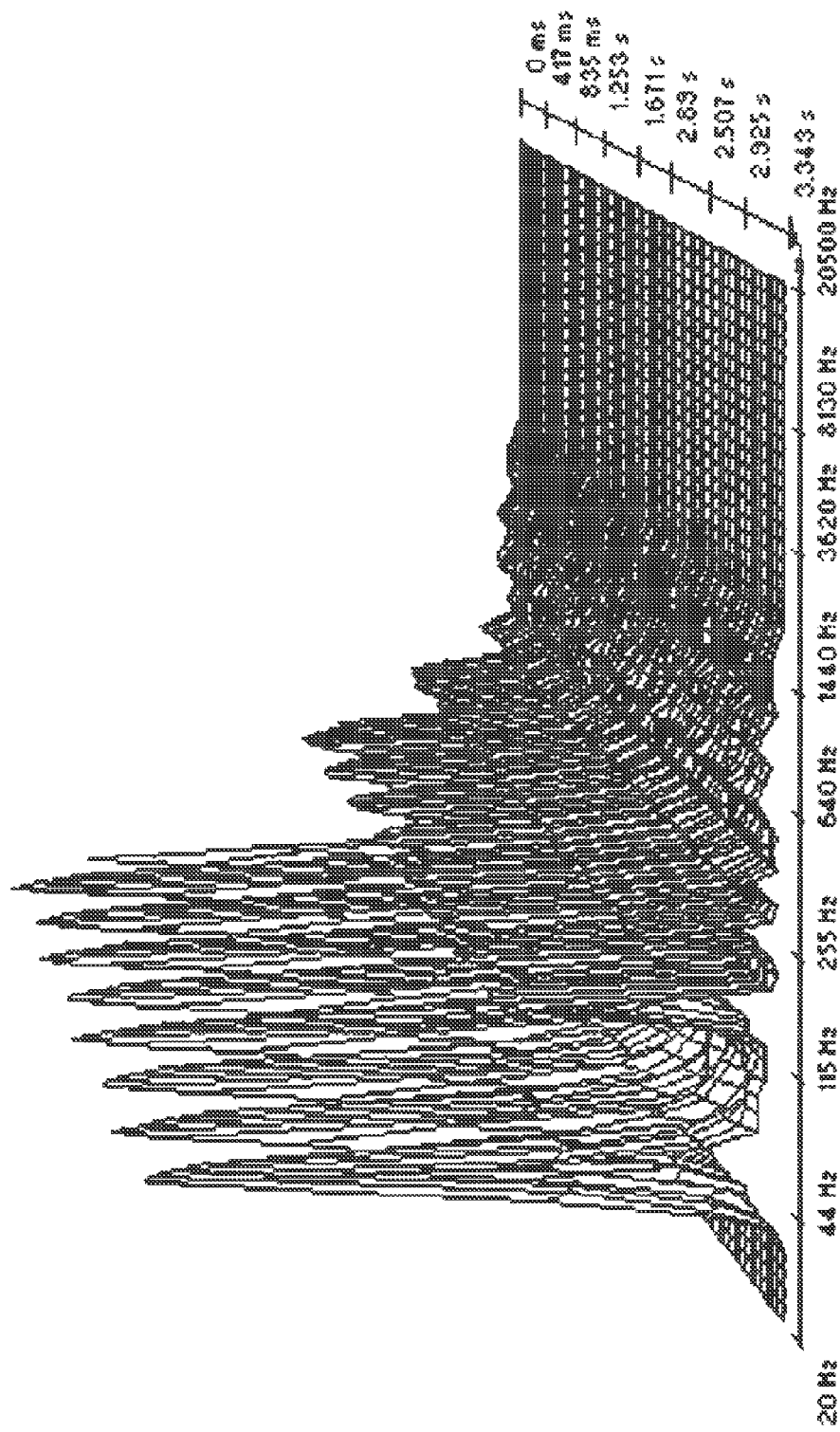
Figure 4D:
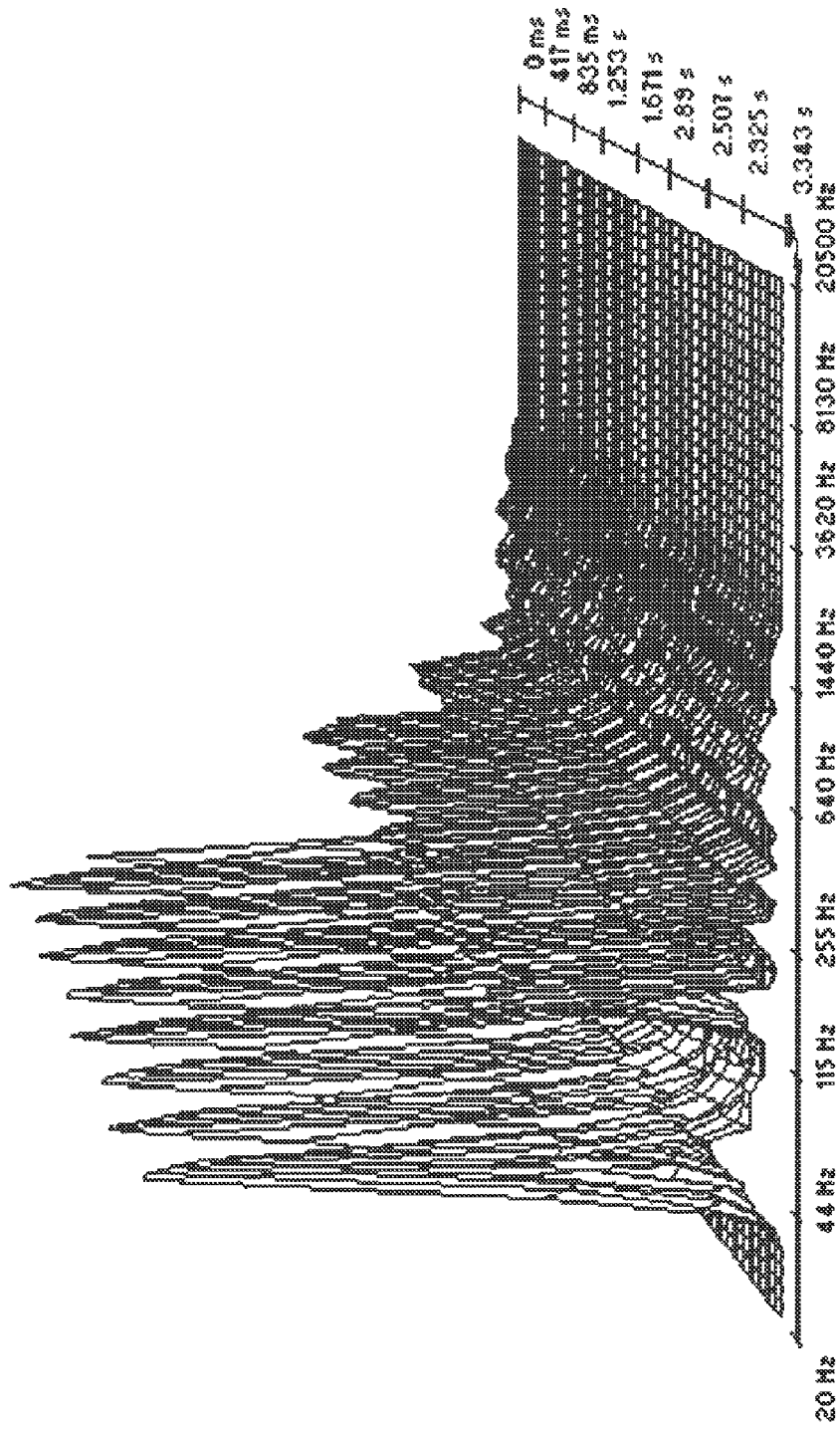
Figure 4E:
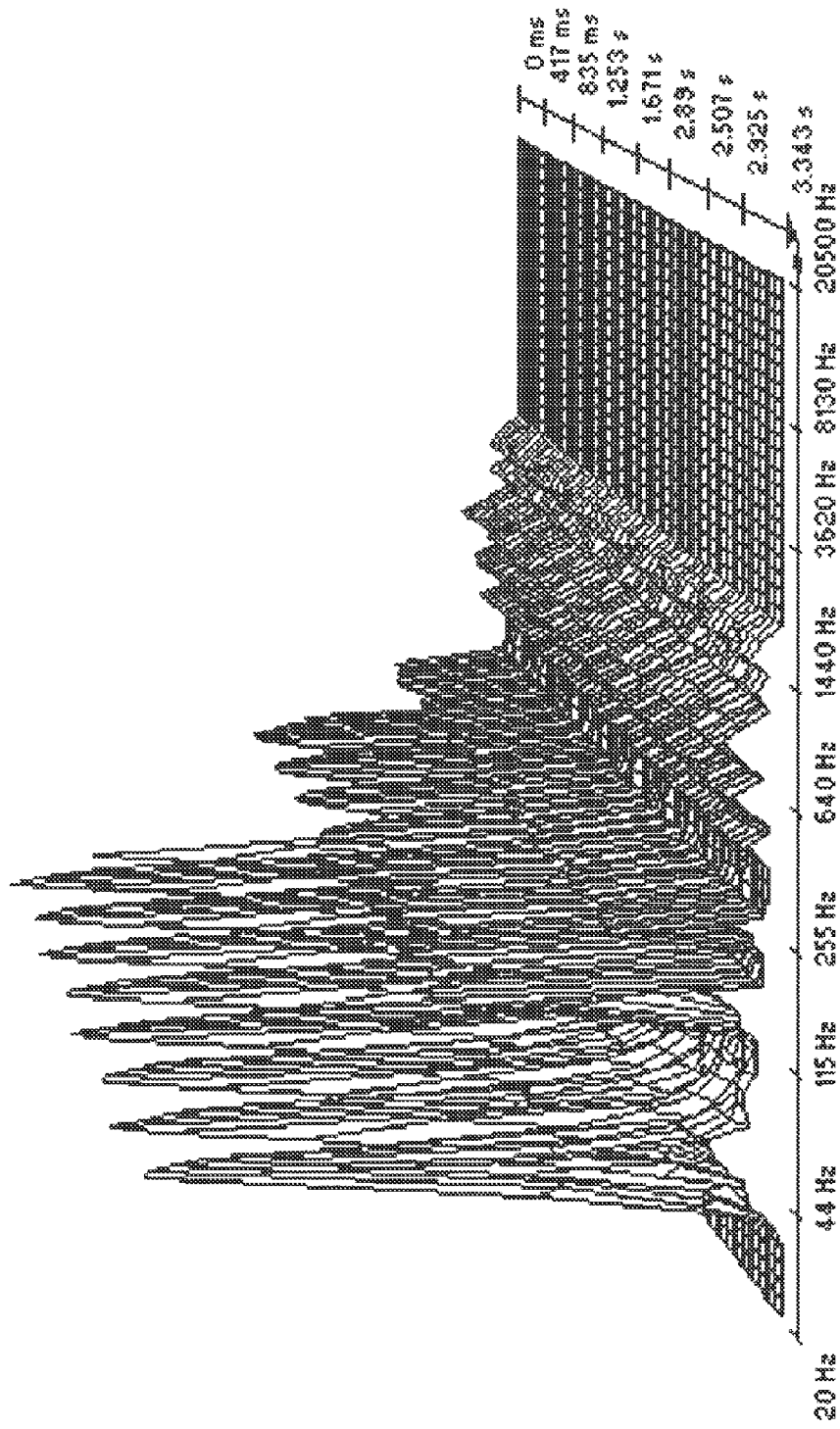
Figure 4G:
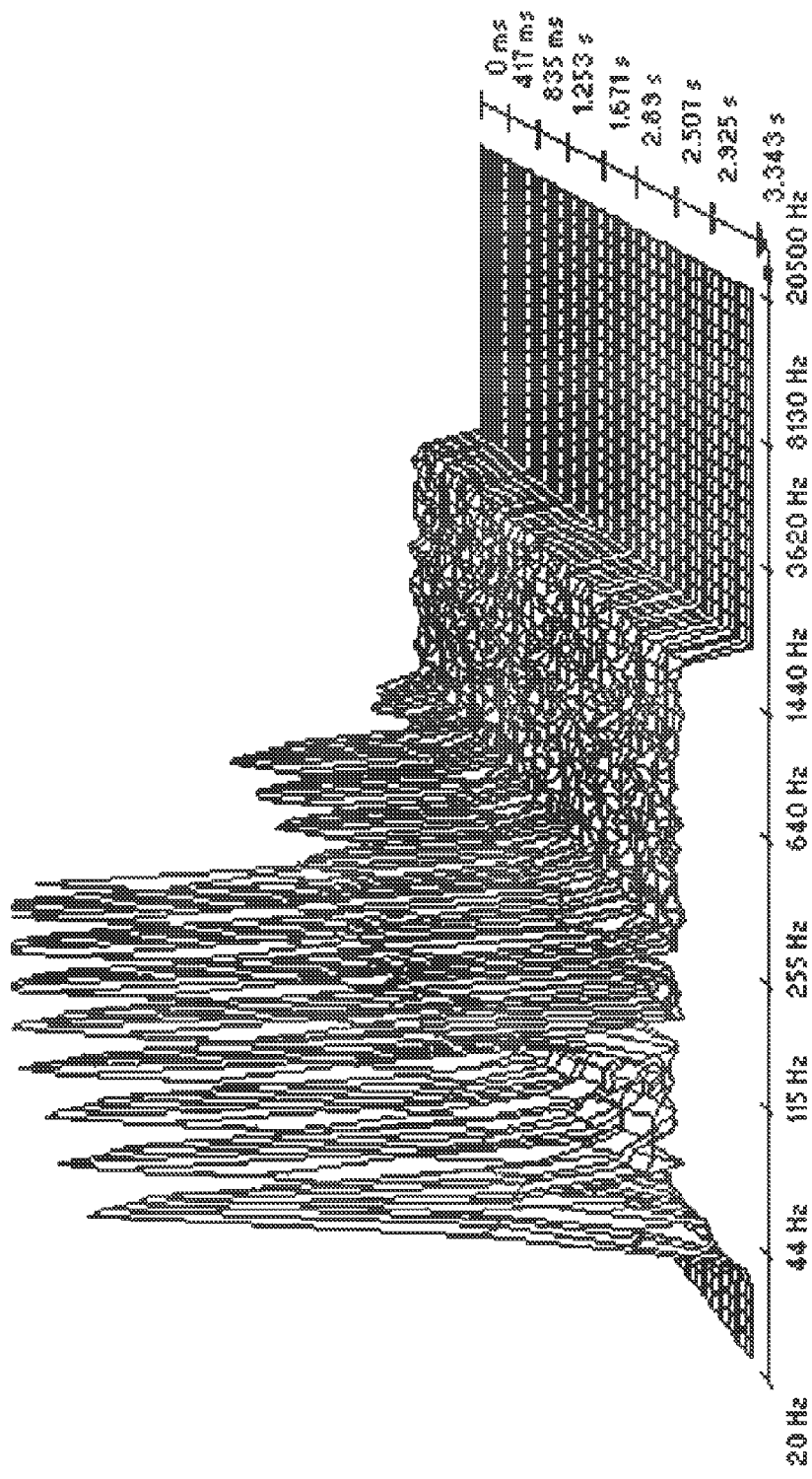
Figure 4H:
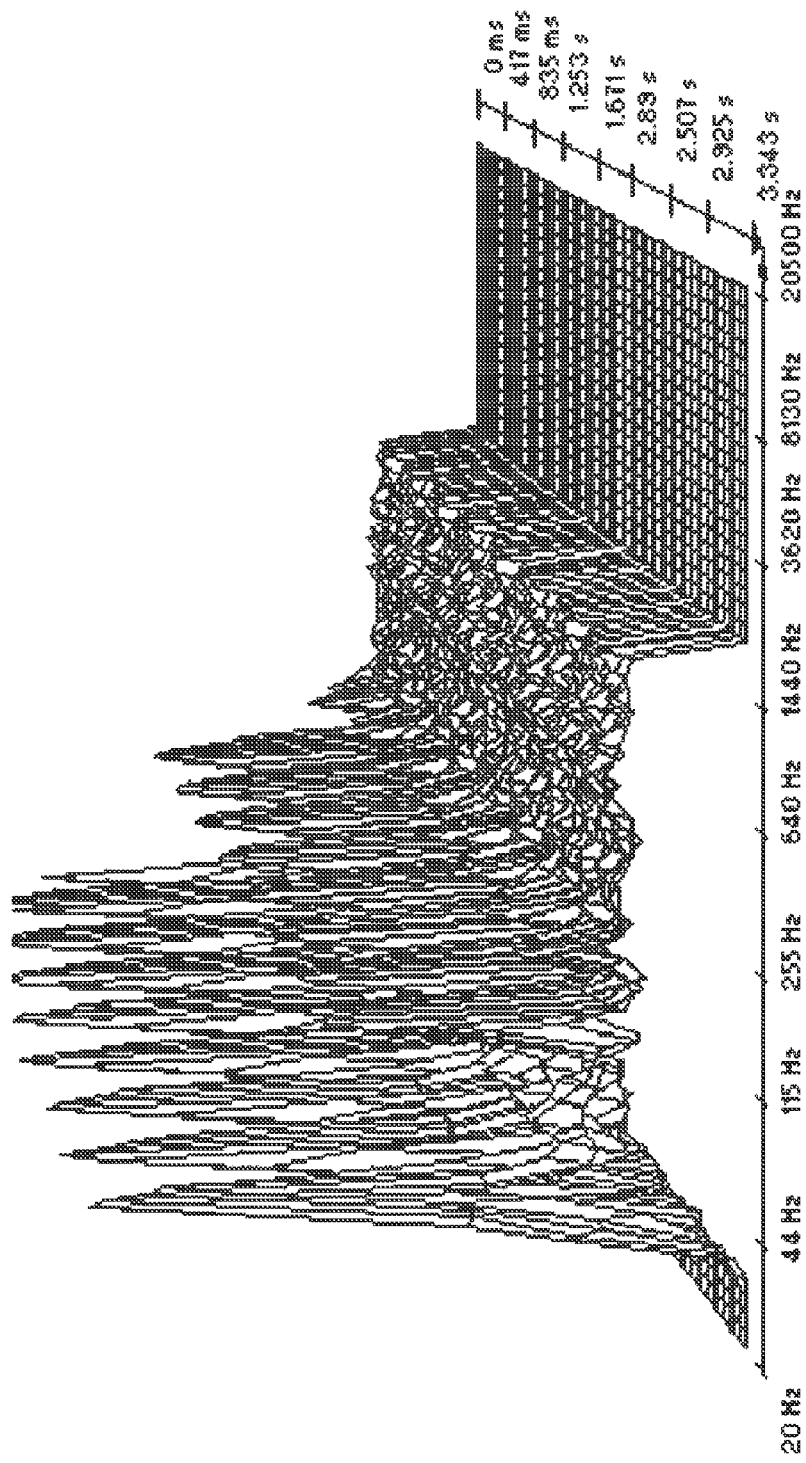
Figure 41:
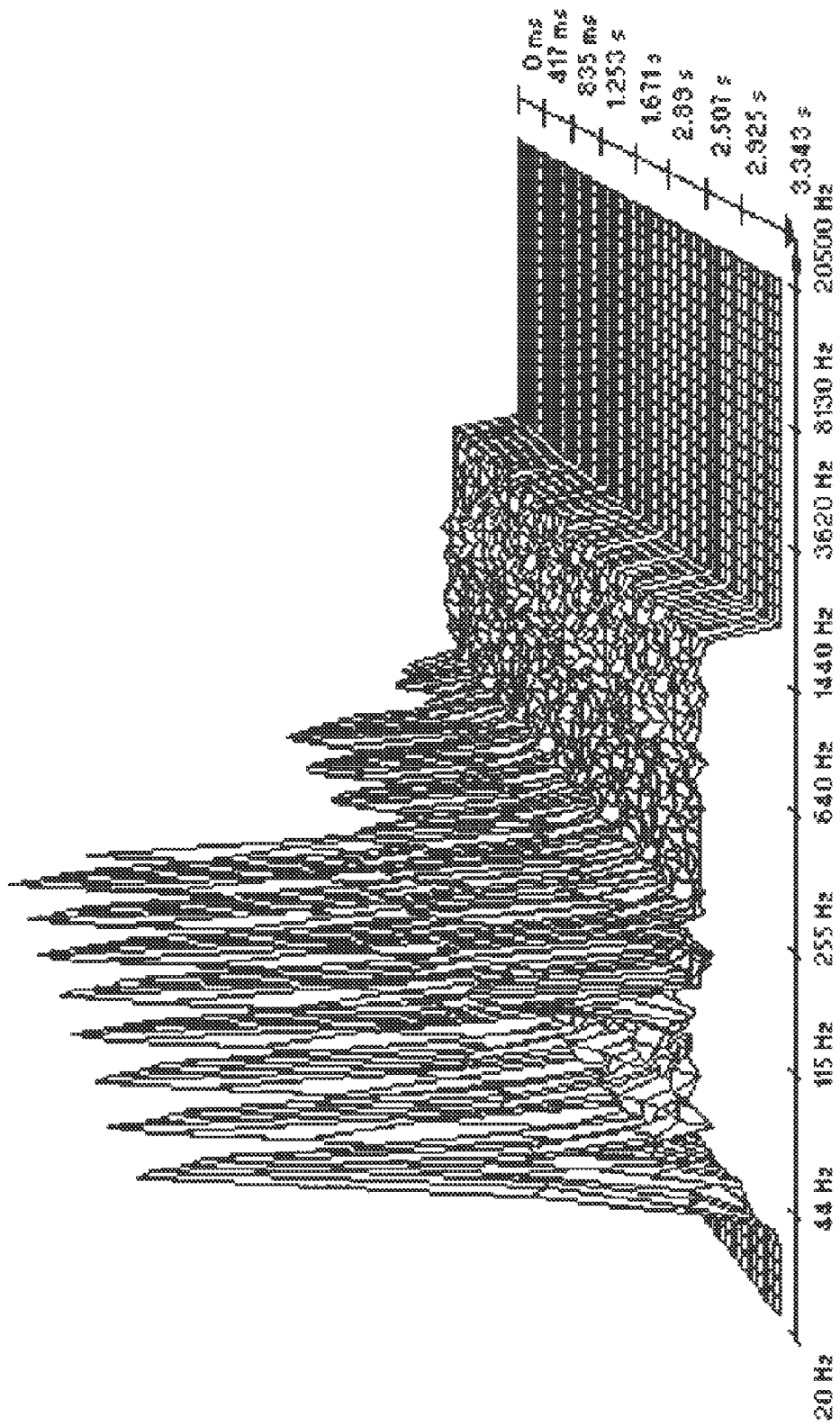
Figure 4J:
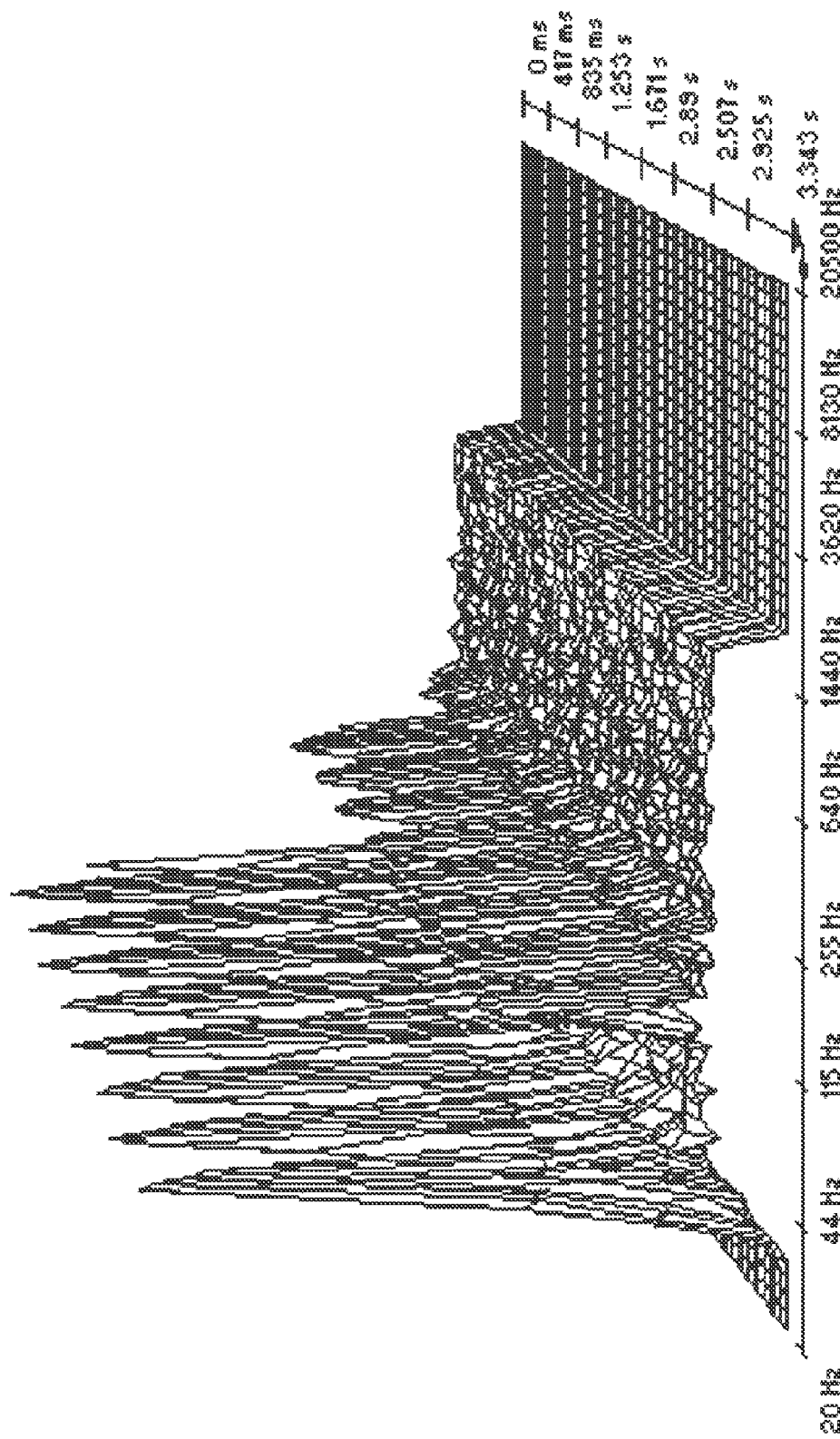
Figure 4K:
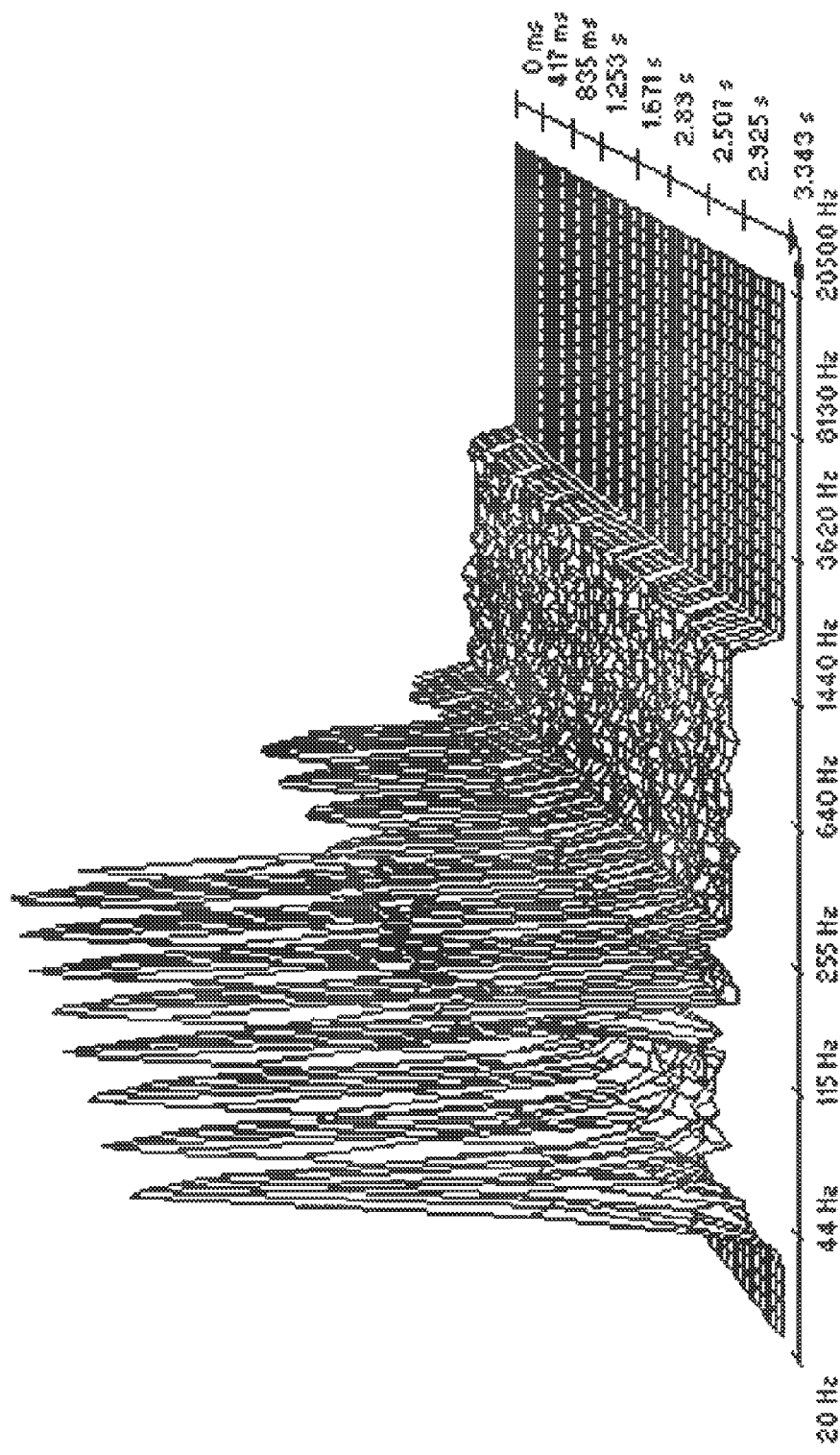
Figure 4L:
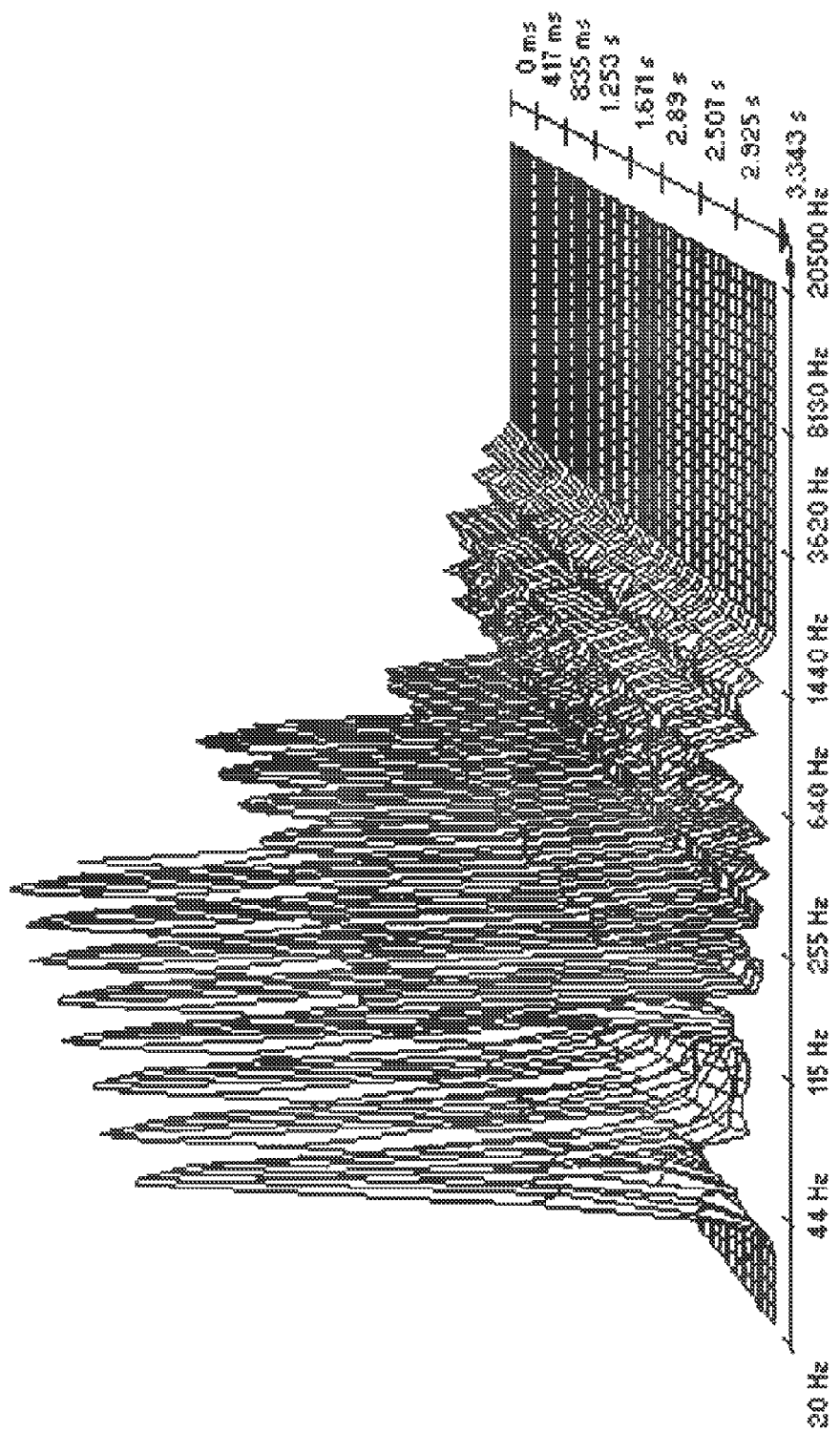
Figure 4M:
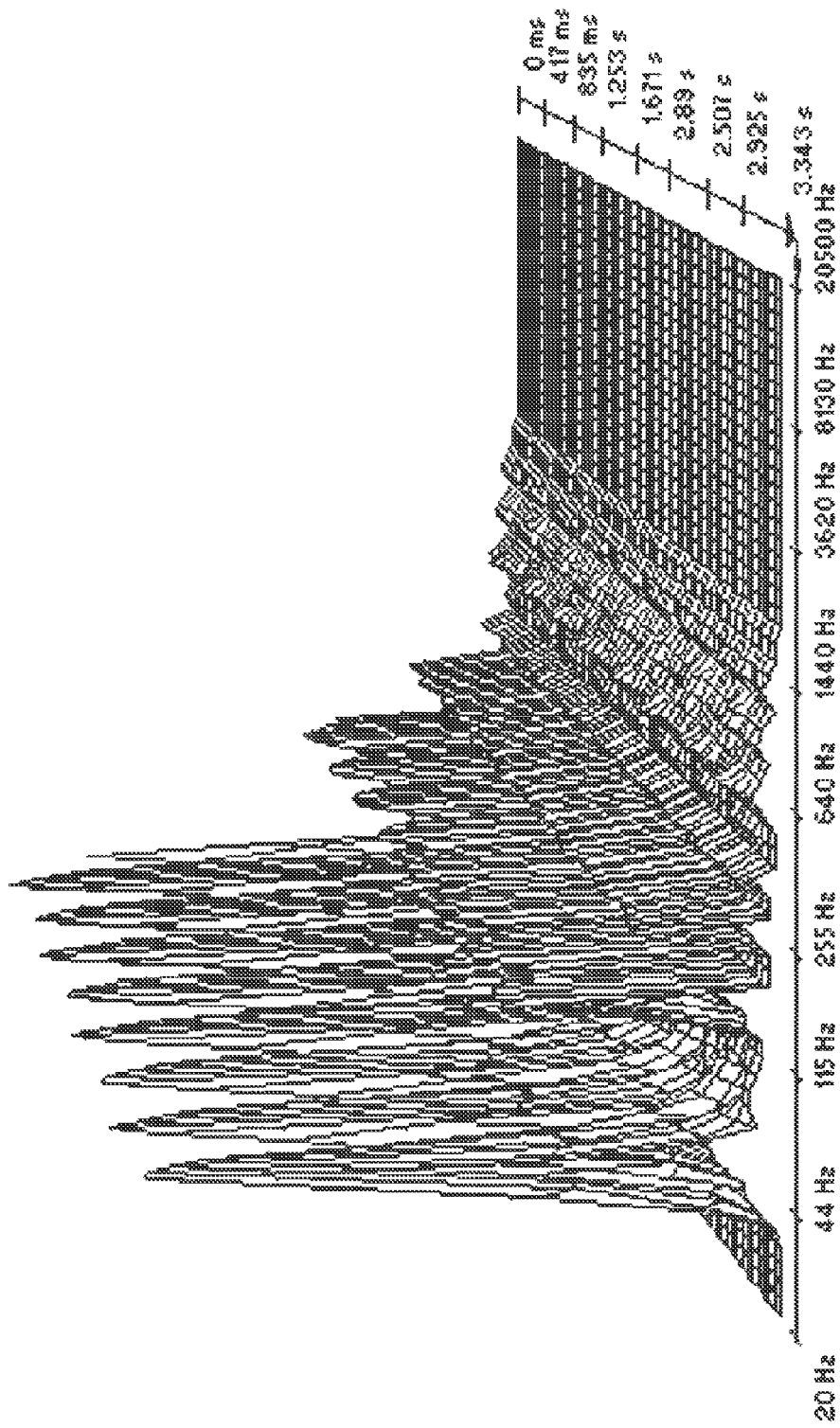
Figure 4N:
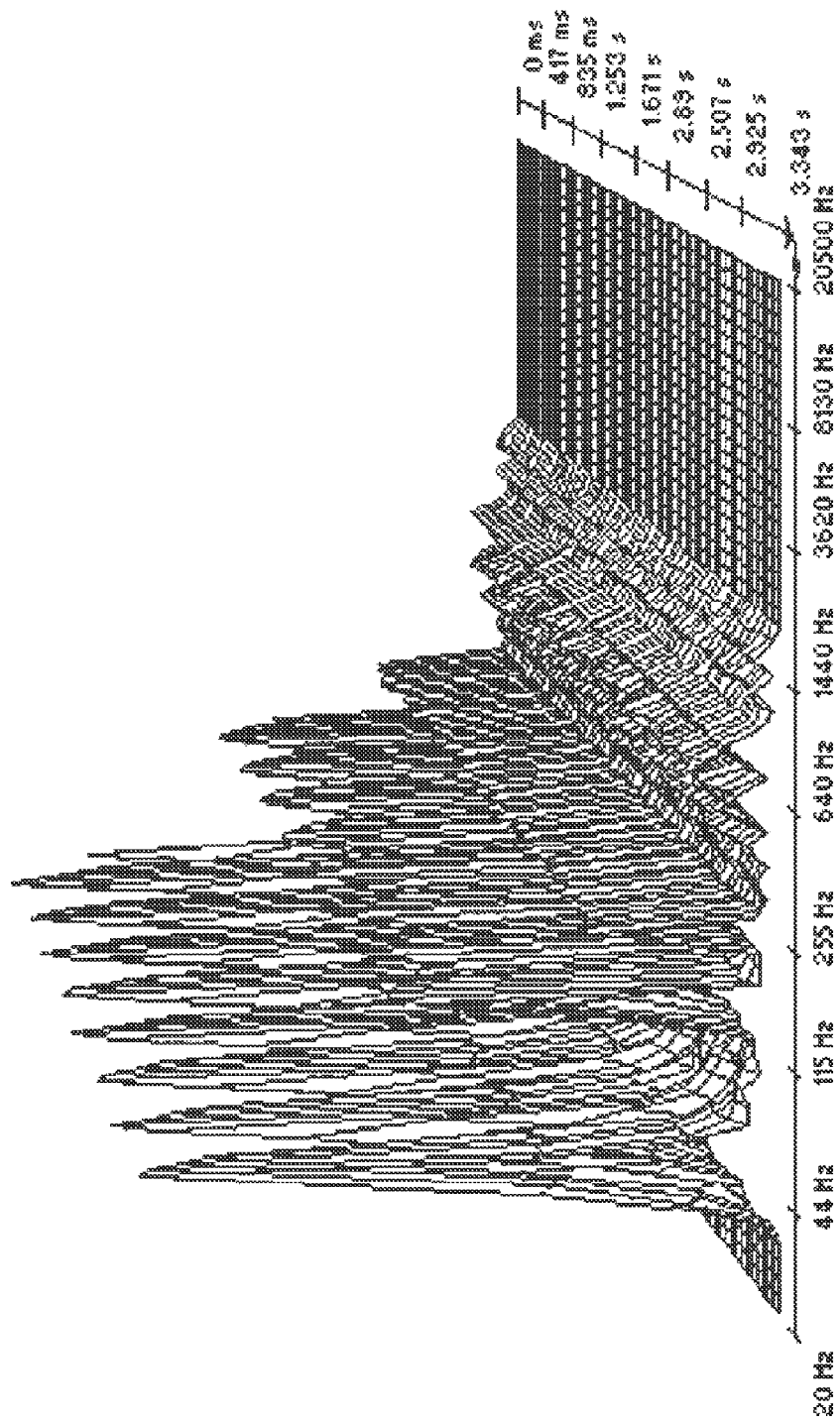
Figure 40:
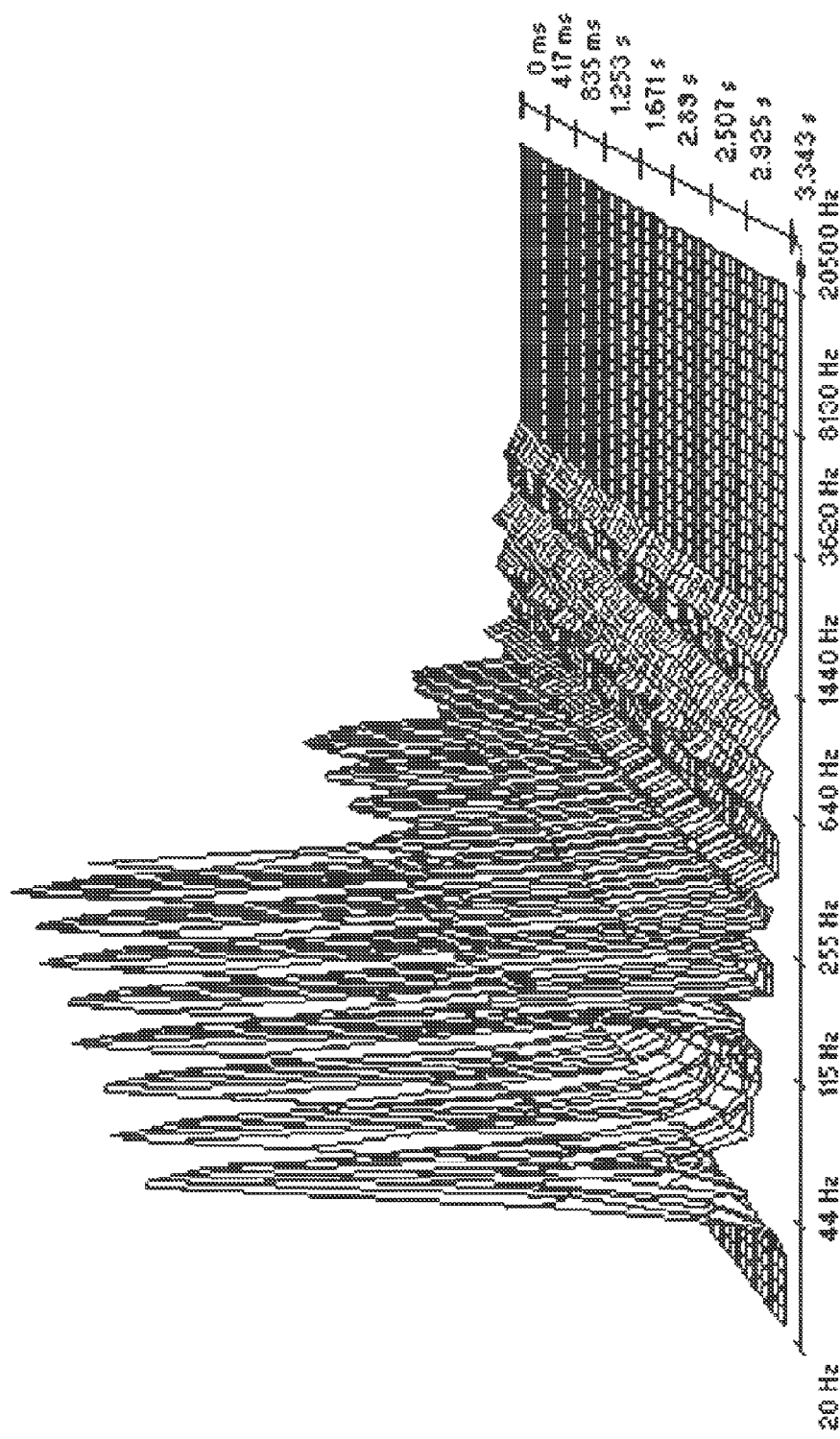

Each dilution tube is placed on the top of a solenoid transforming changes in the magnetic field into an electric current. The current is amplified 500 times by a Sound-Blaster® card and analyzed on a computer employing three software applications: one for direct recording of the waves, and two for performing Fourier analysis of the harmonics, as shown in FIGS. 4A-4O.

A positive signal is generally defined by an increase of higher frequencies (500-3,000 Hz) over the respective background sample, though the criteria may be different for different types of analysis; that is, using a Fourier analysis, the positive experimental show a significant difference from control with respect to an increase in signal energy in the 500-3,000 Hz band. Using other analysis techniques, the definition of a positive result will correspondingly be different.

Usually positive signals are found in the range of the $10^{-7}$ to $10^{-13}$ dilutions. At high dilutions (from $10^{-12}$), calculations indicate that there is no DNA left and that the EMS should come for self-maintained nanostructures induced in water by the DNA from which they originated.

3) Effect of DNAse:

Destruction of DNA sequences by DNAse abolishes their capacity to induce EMS in water. Since the nanostructures formed in water are fully resistant to DNAse, but are sensitive to heat, the DNAse effect is shown according to the following protocol, designed to suppress this secondary source of EMS. The DNA preparation is heated at 100° C. for 30 min to destroy the nanostructures. After cooling at 37° C., DNAse I at a final concentration of 10 U/μg of DNA is added to the DNA solution and incubated in the presence of 5 mM $MgCl_2$ for 16 Hours at 37° C. An aliquot of untreated DNA solution is kept as a positive control. The DNAse treated preparation is completely devoid of EMS emission at any dilutions. Therefore the main source of EMS is DNA.

4) Nature of the DNA sequences at the origin of EMS:

A survey of the main bacteria species involved in human infections indicated that the following species are producing signals, either as pure culture suspension, or as DNA:

*Escherichia coli* (strain K1)
*Streptococcus* B
*Staphylococcus aureus*
*Proteus mirabilis*
*Pseudomonas aeruginosa*
*Bacillus aeruginosa*
*Mycoplasma pirum*

Figure 2A:
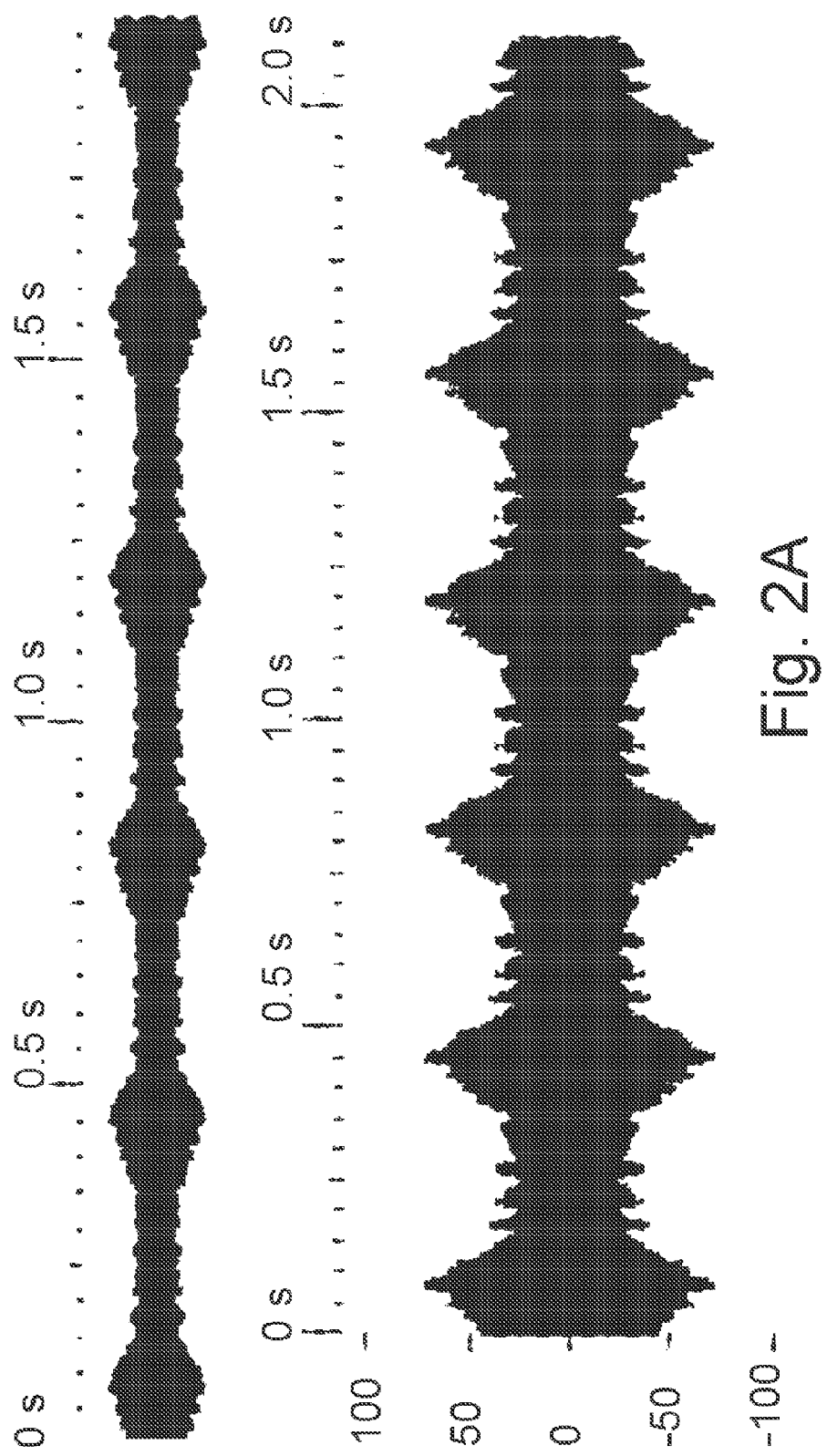
FIGS. 2A-2O show, respectively time domain electromagnetic signals (EMS) emitted over 6 seconds by serial decimal dilutions from $10^{-2}$ to $10^{-15}$ of a solution (filtered through a 100 nm pore size filter, except FIG. 2O, which was unfiltered).
Figure 2B:
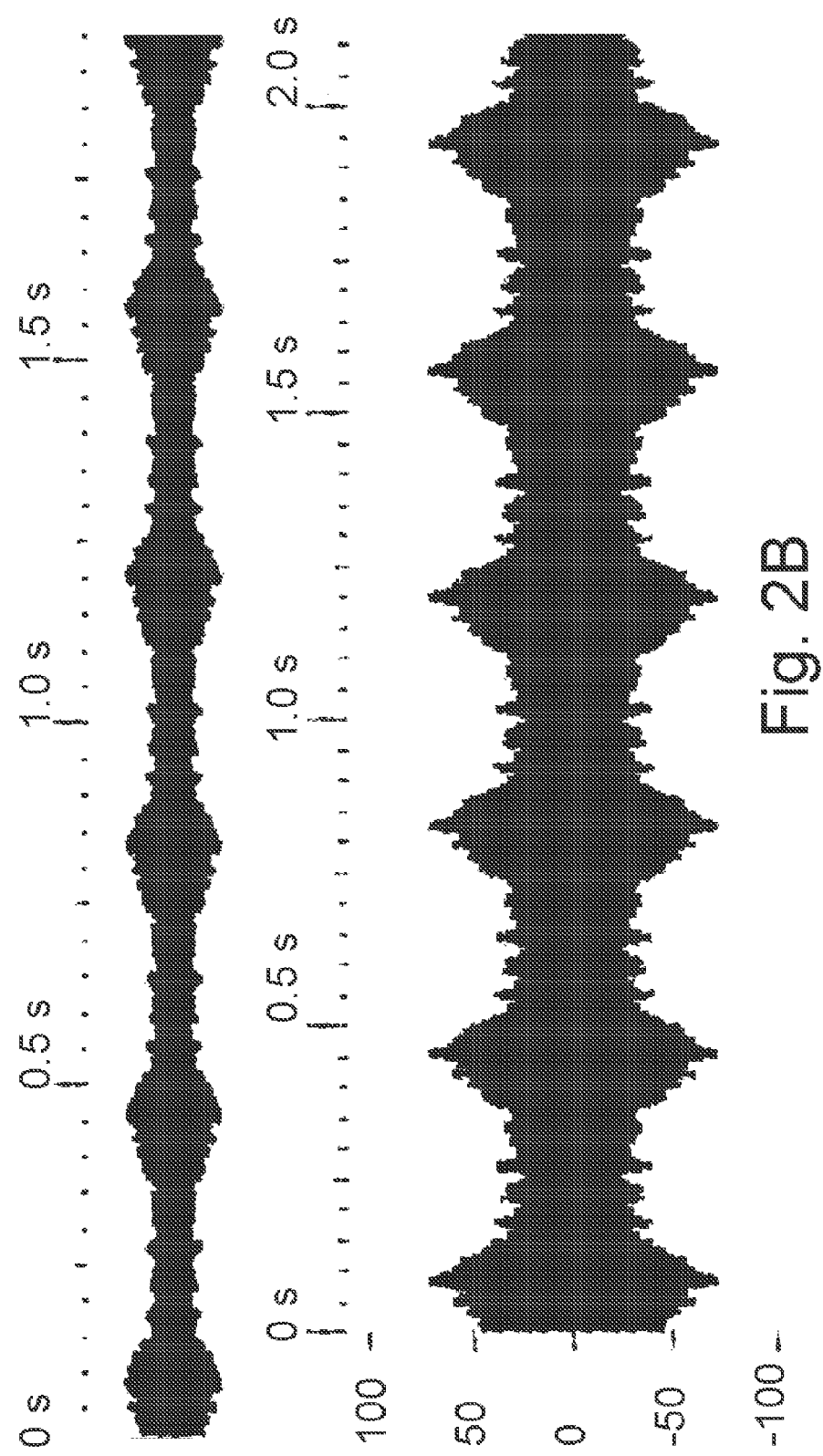
Figure 2C:
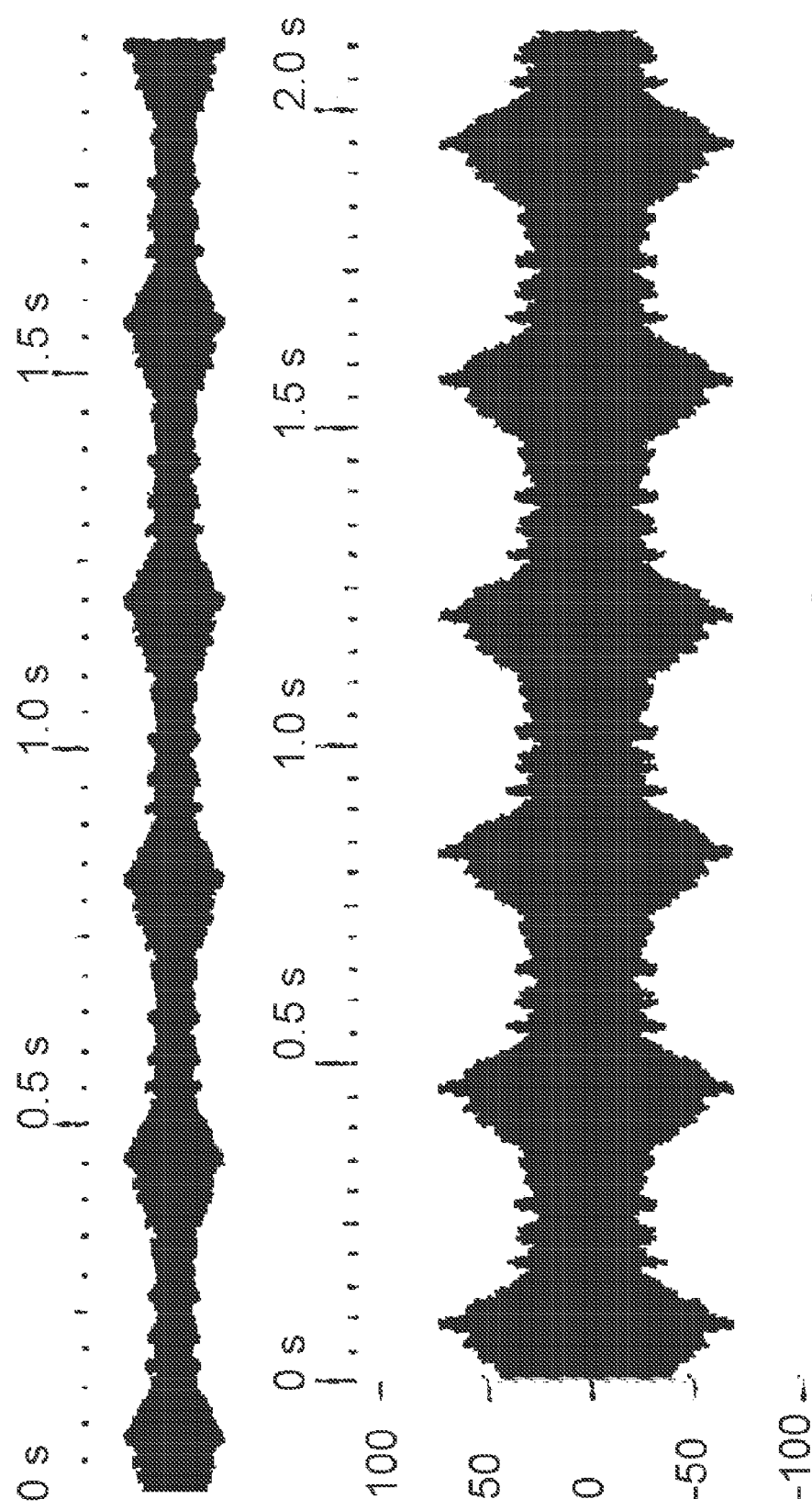
Figure 2D:
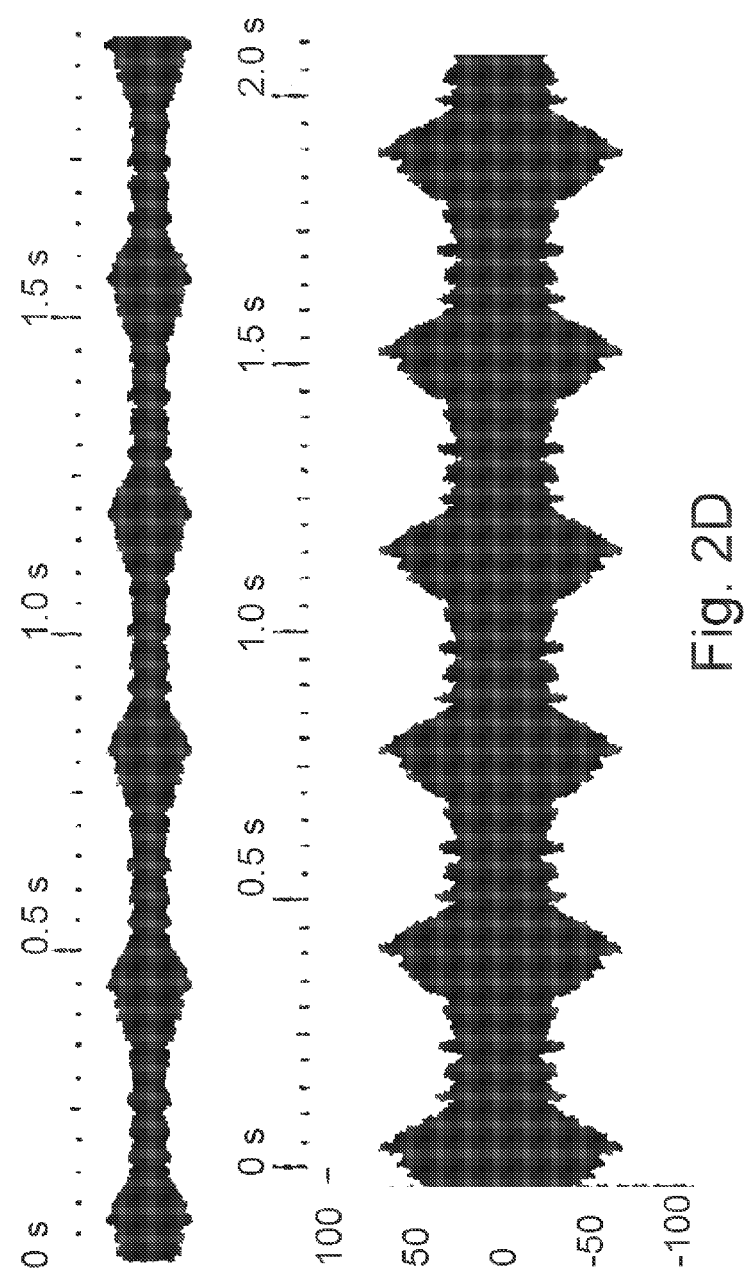
Figure 2E:
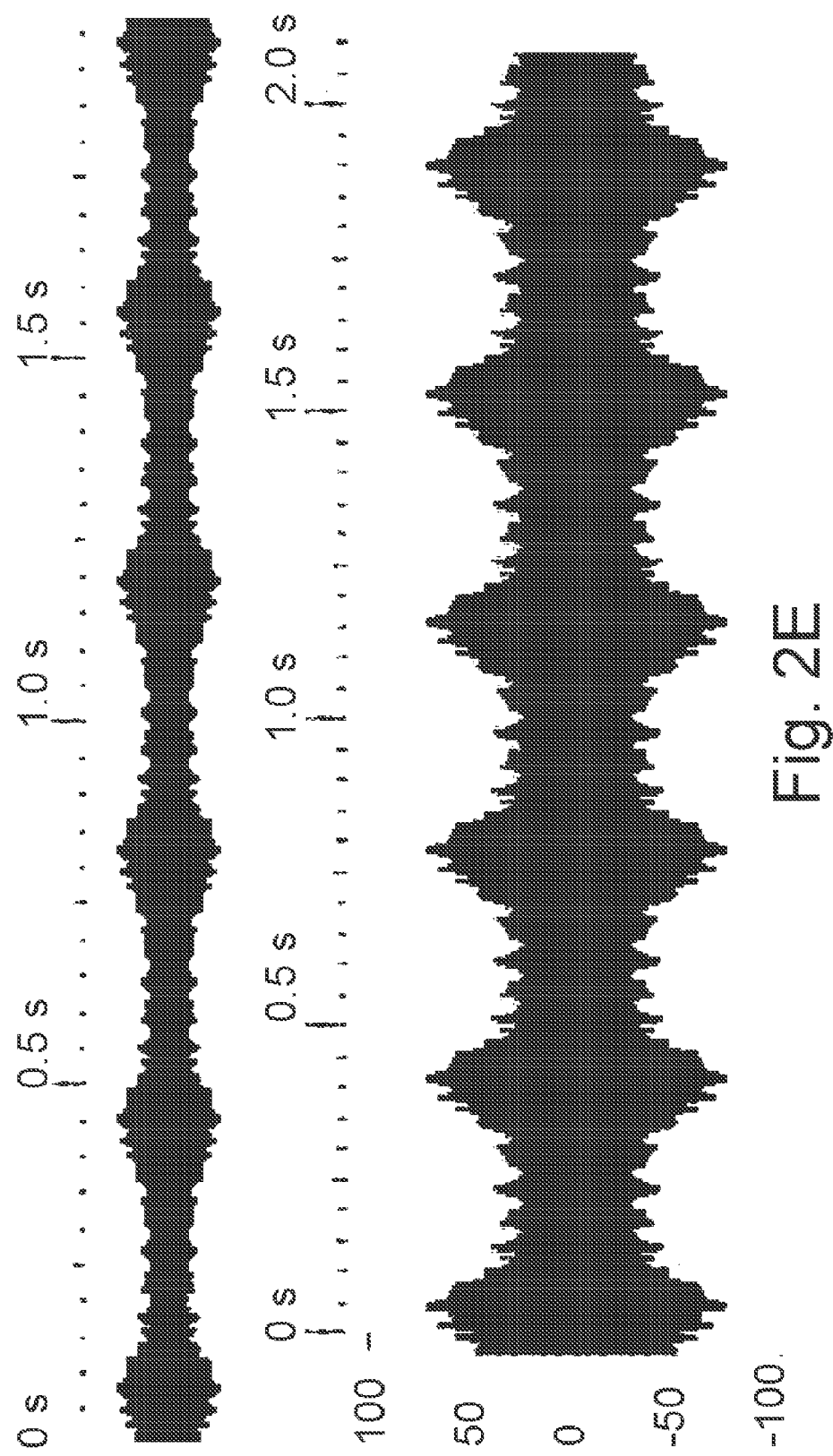
Figure 2F:
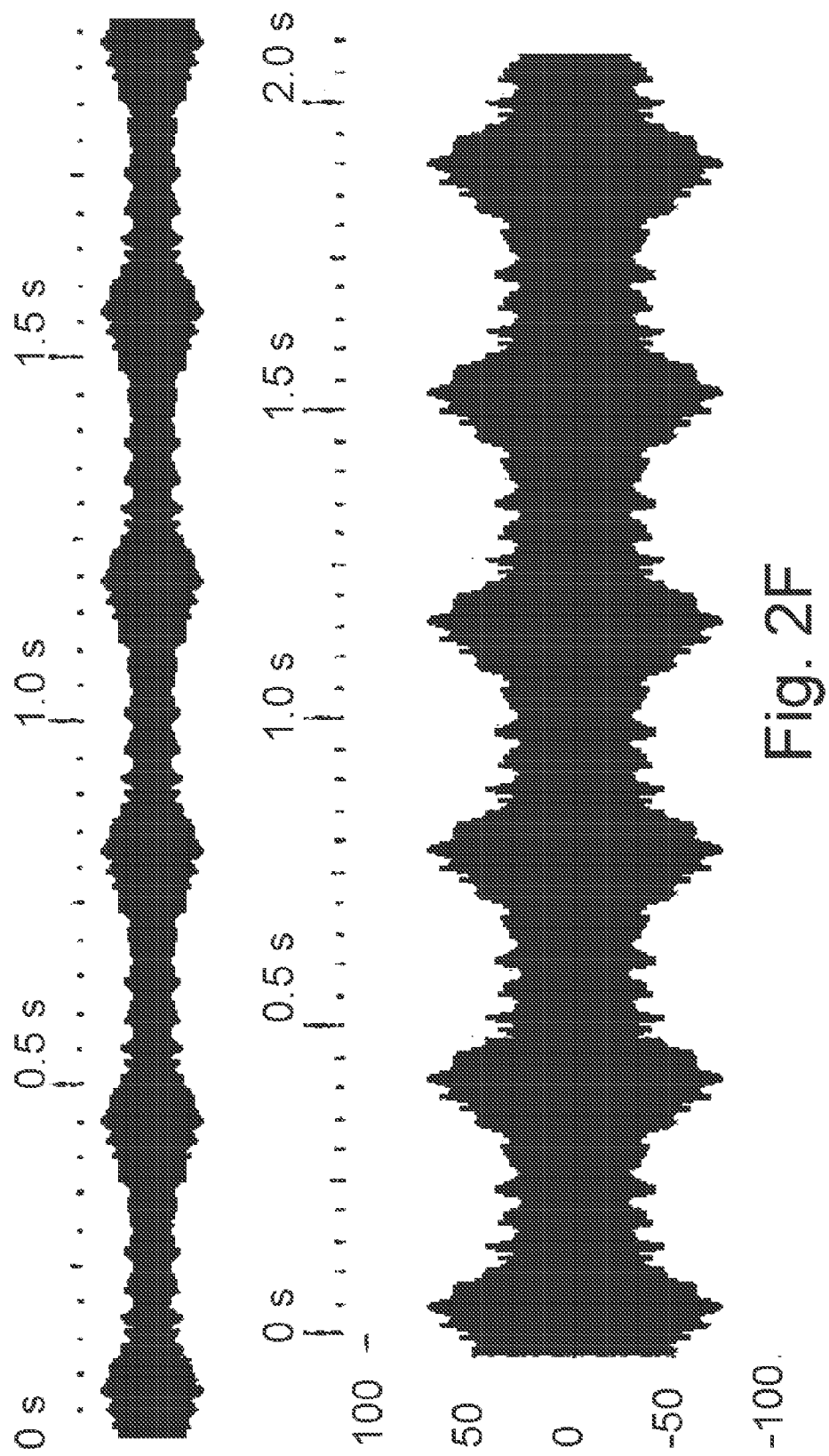
Figure 2G:
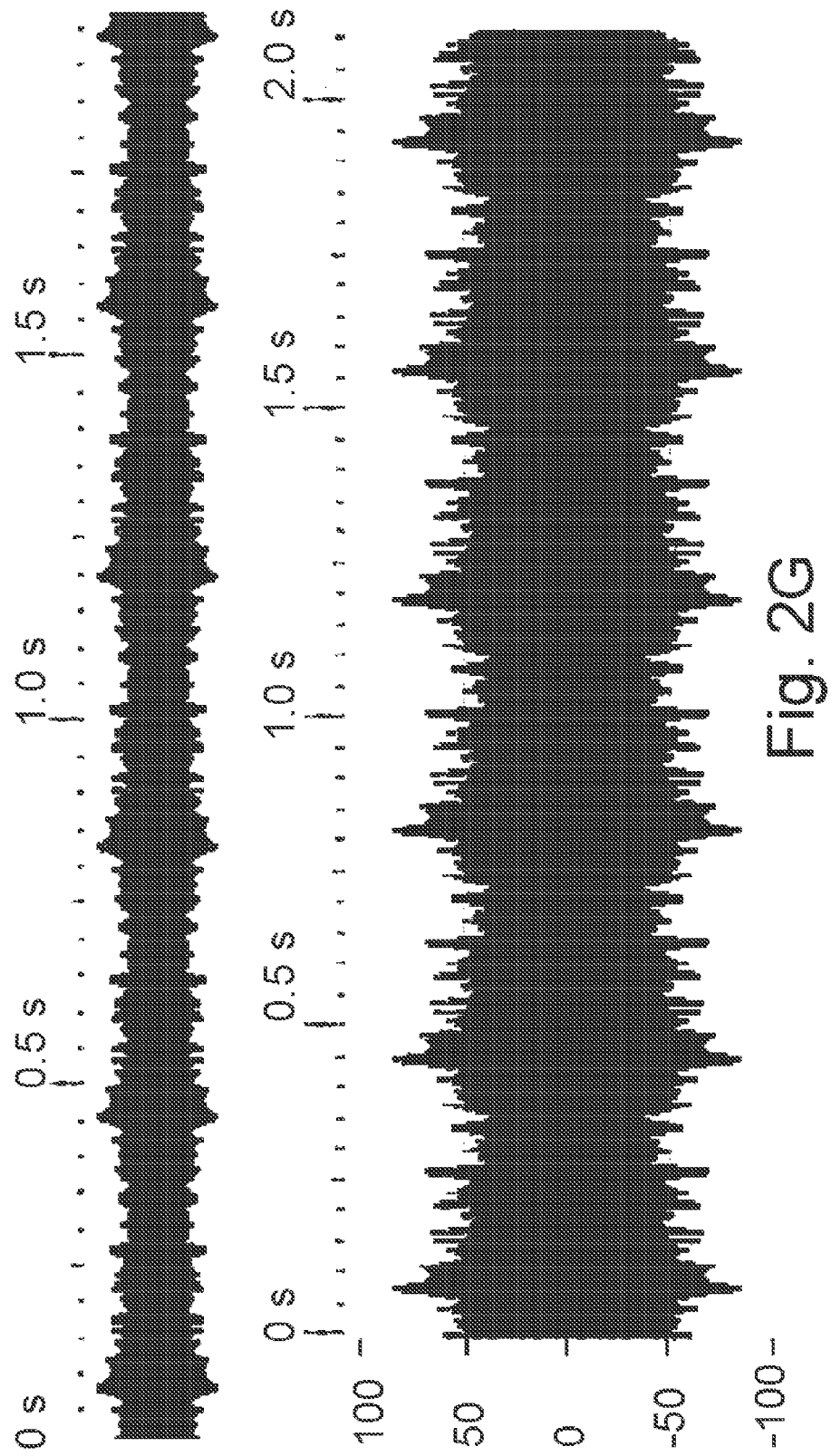
FIGS. 2G, 2H, 2I, 2J, 2K, are dilutions of a filtered solution of DNA extracted from E. Coli K1.
Figure 2H:
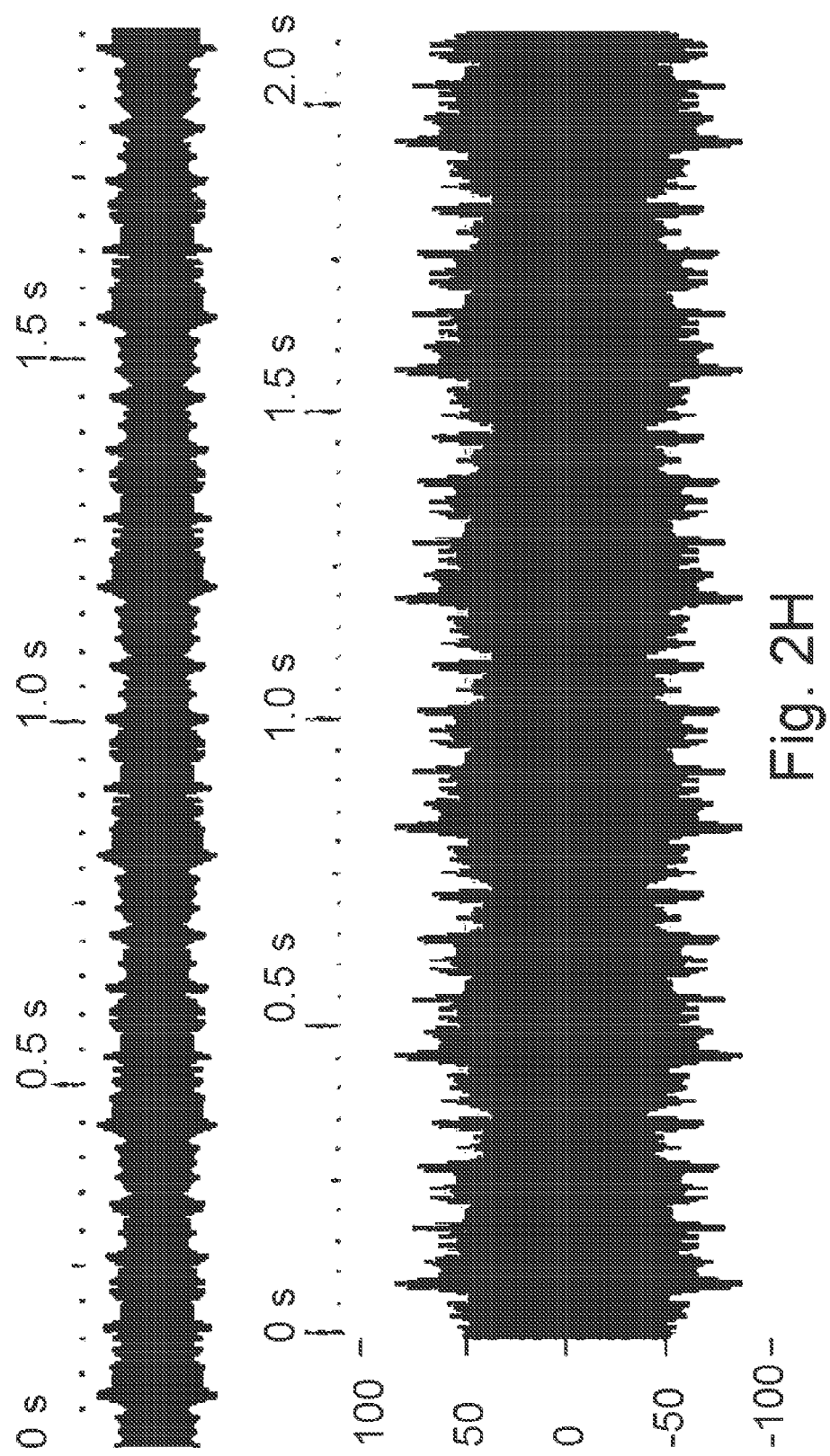
Figure 2I:
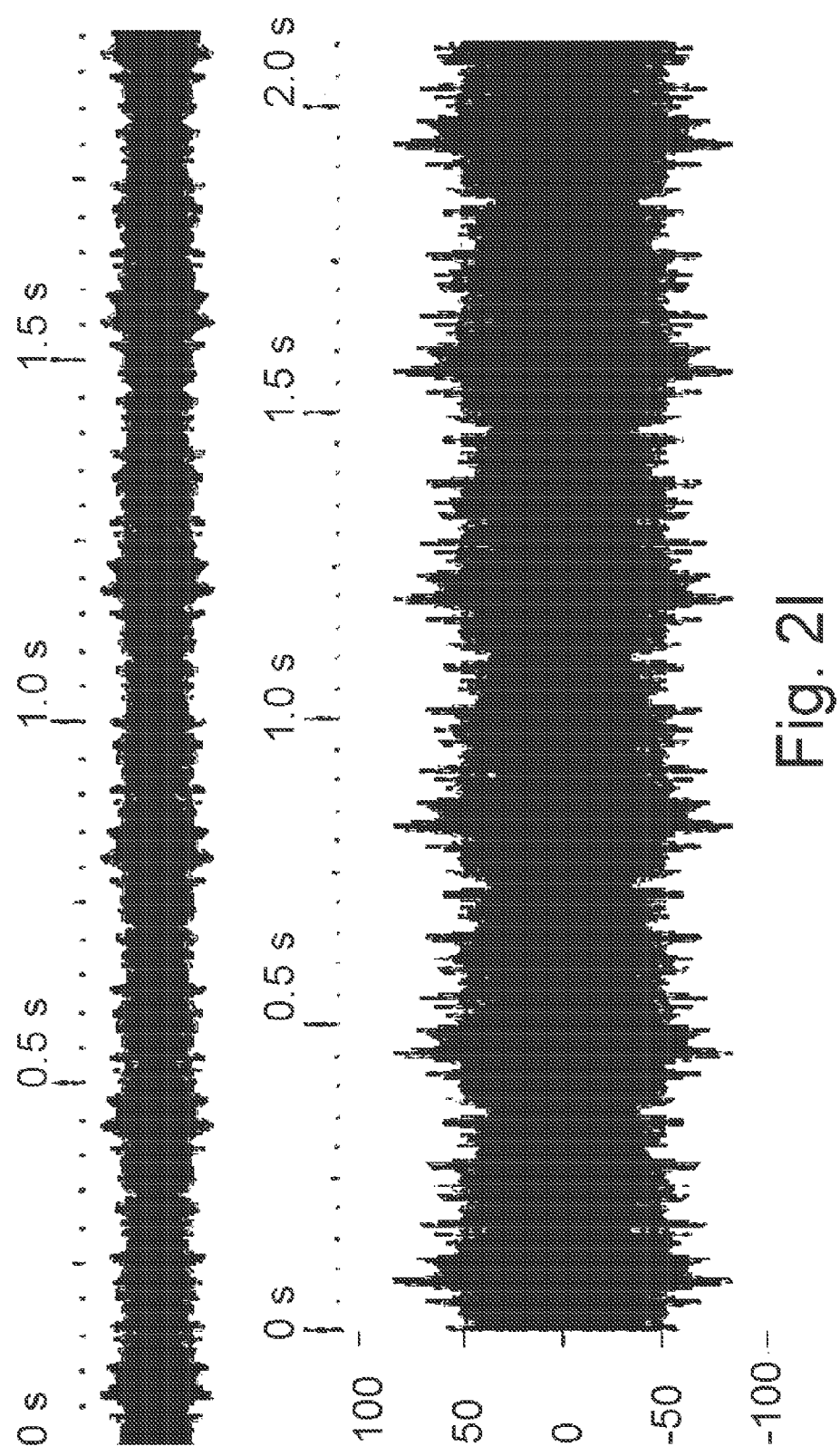
Figure 2J:
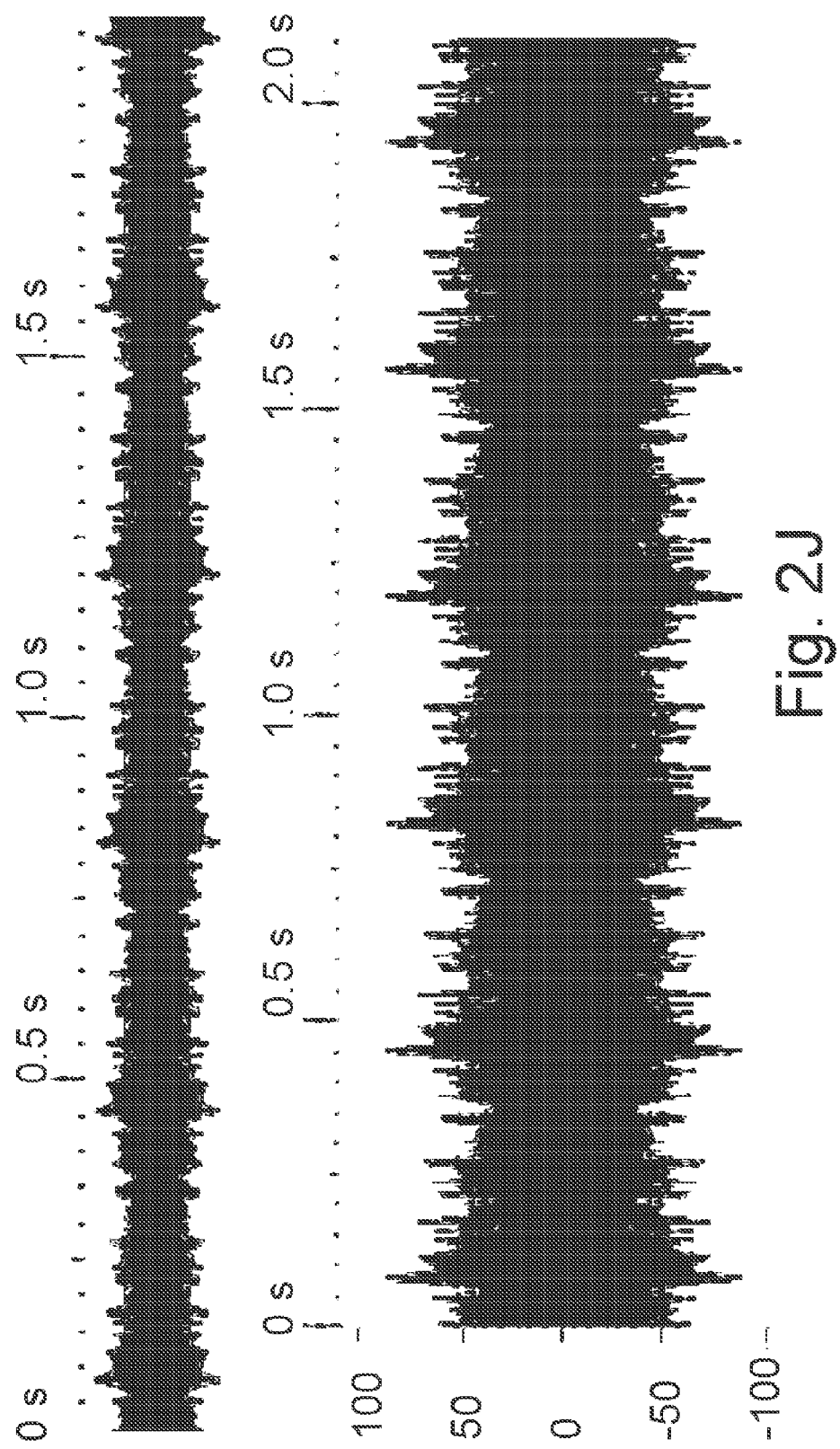
Figure 2K:
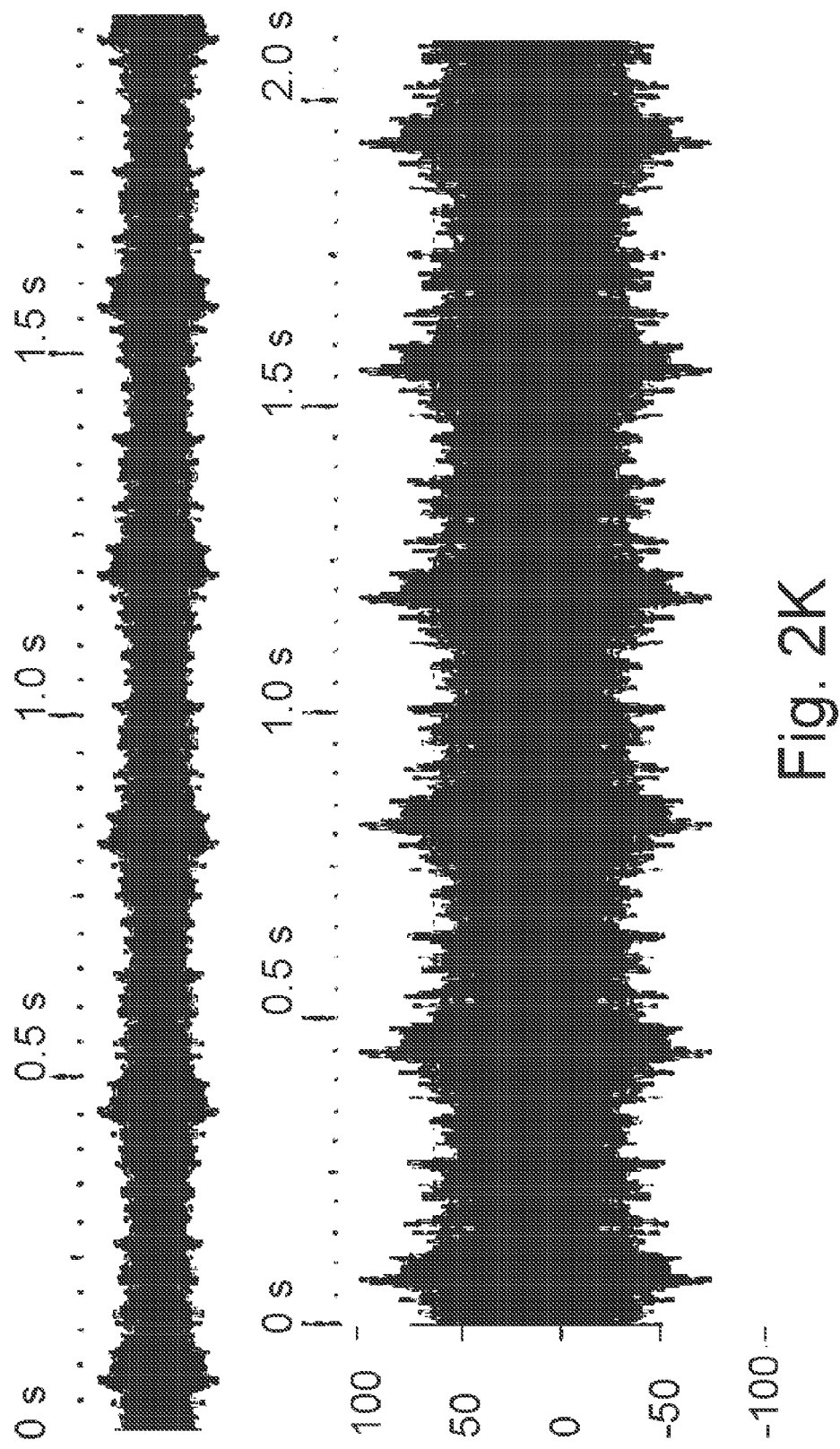
Figure 2L:
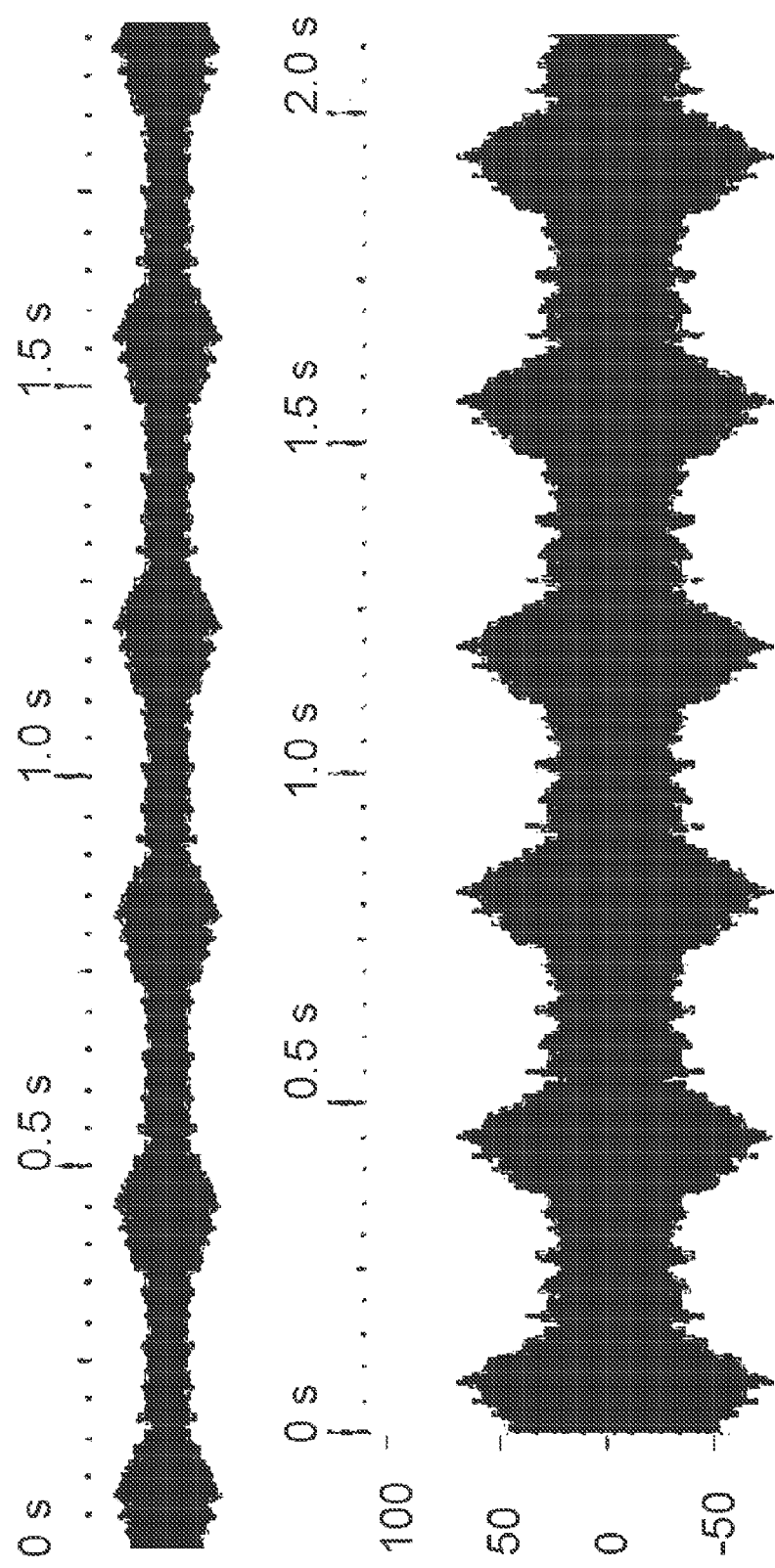
Figure 2M:
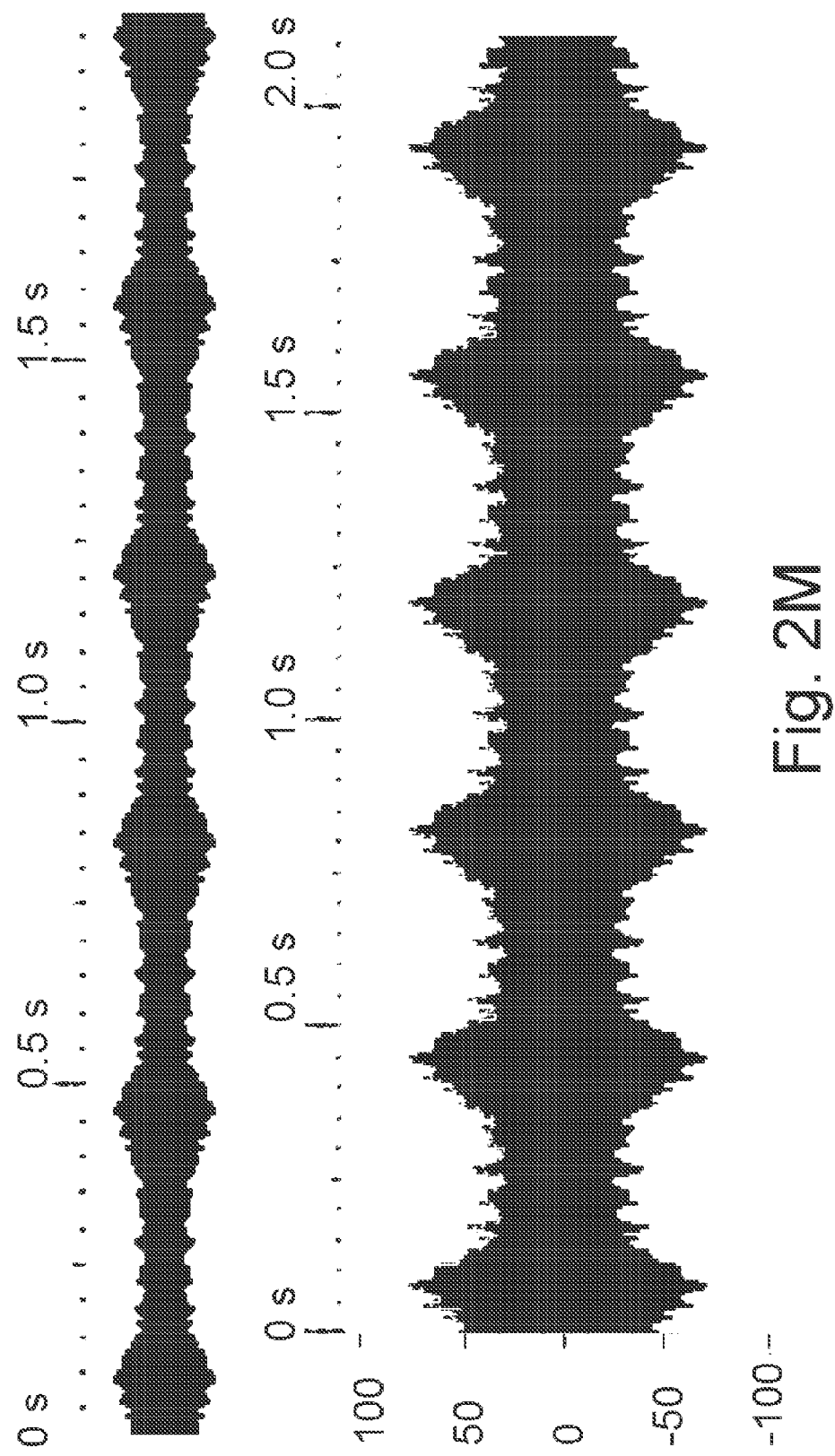
Figure 2N:
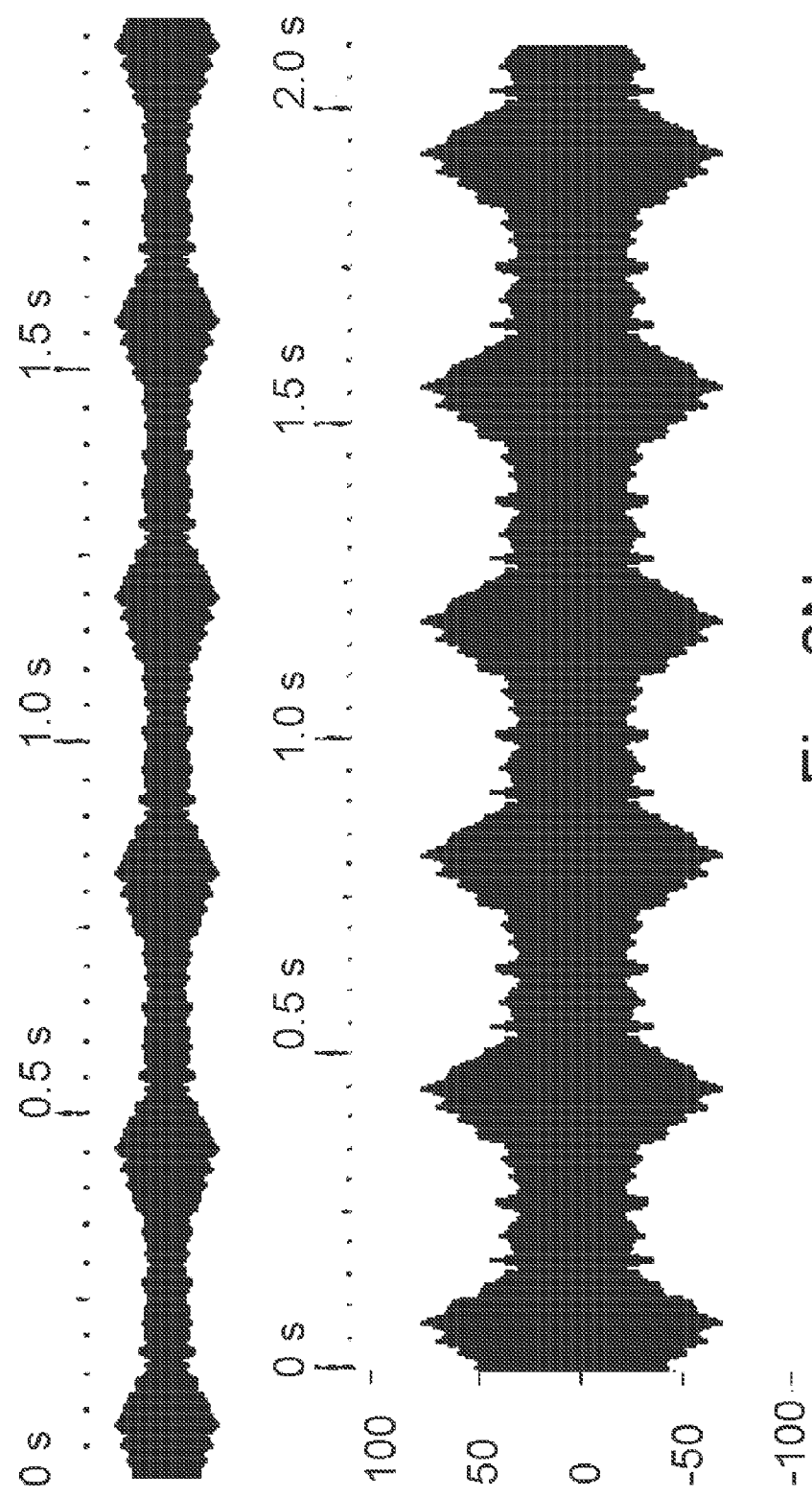
Figure 2O:
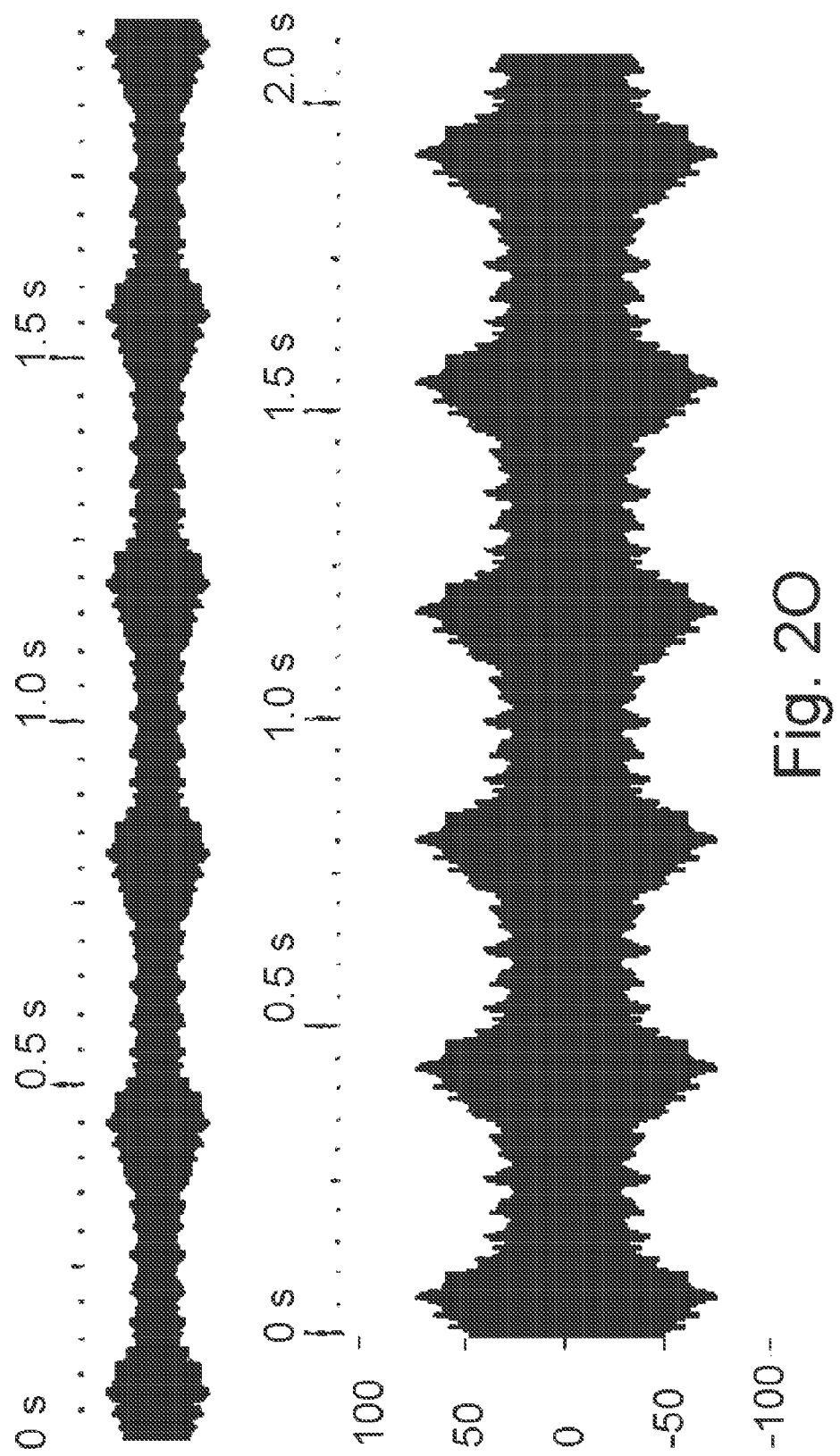
Figure 3A:
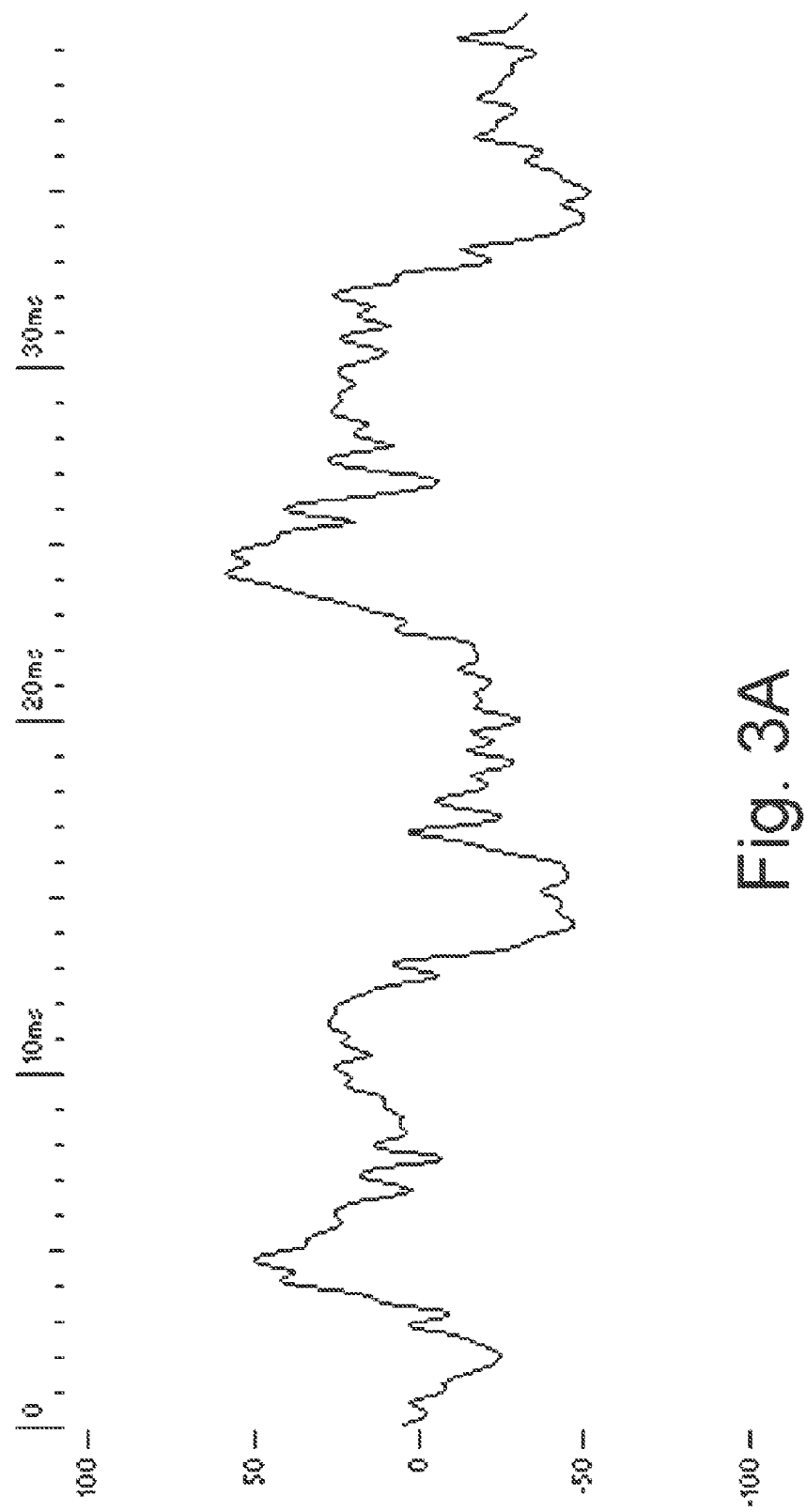
FIGS. 3A-3O show, respectively, show a zoom analysis (millisecond scale) of one part of the recording shown of a respective dilution EMS signal shown in FIGS. 2A-2O.
Figure 3B:
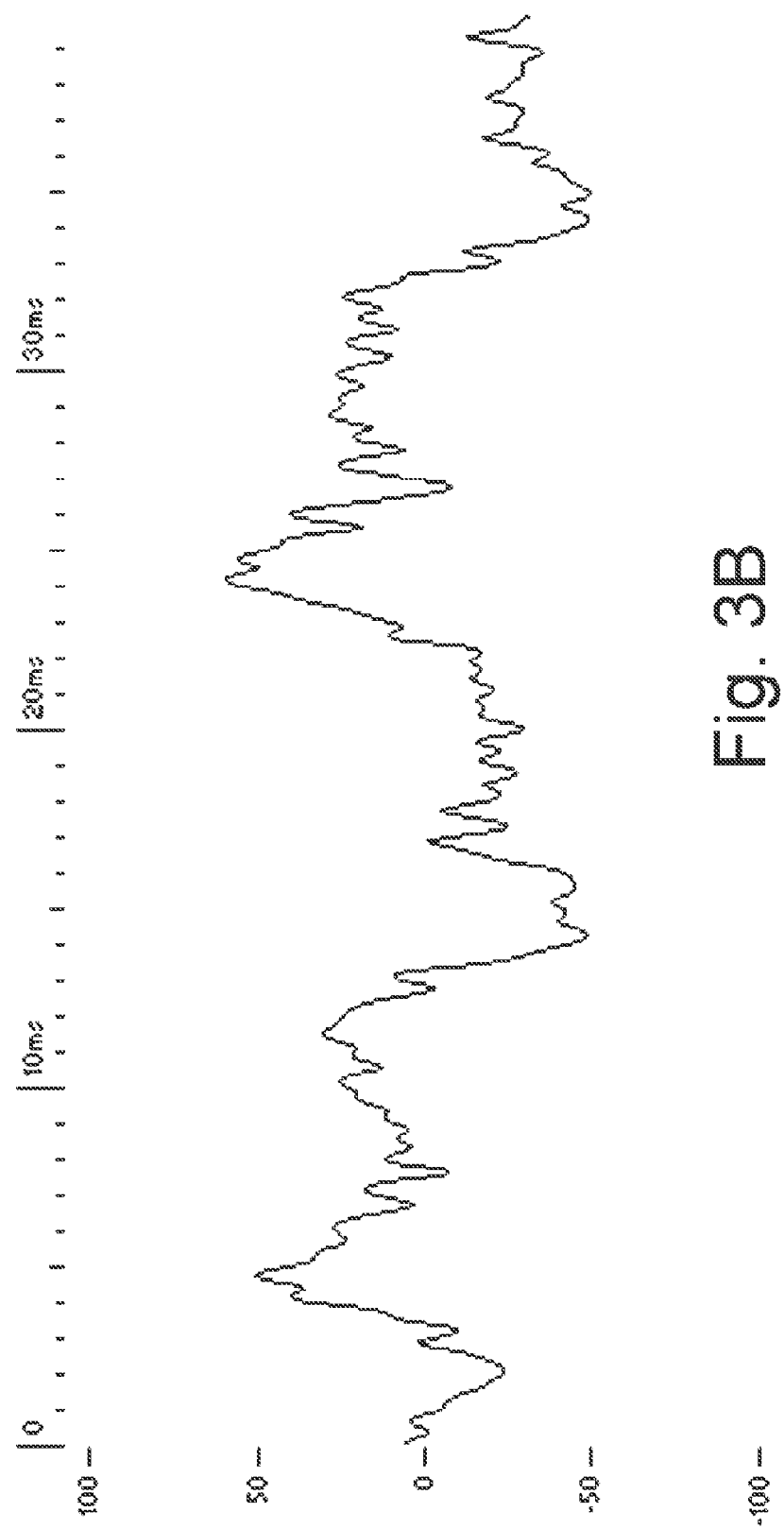
Figure 3D:
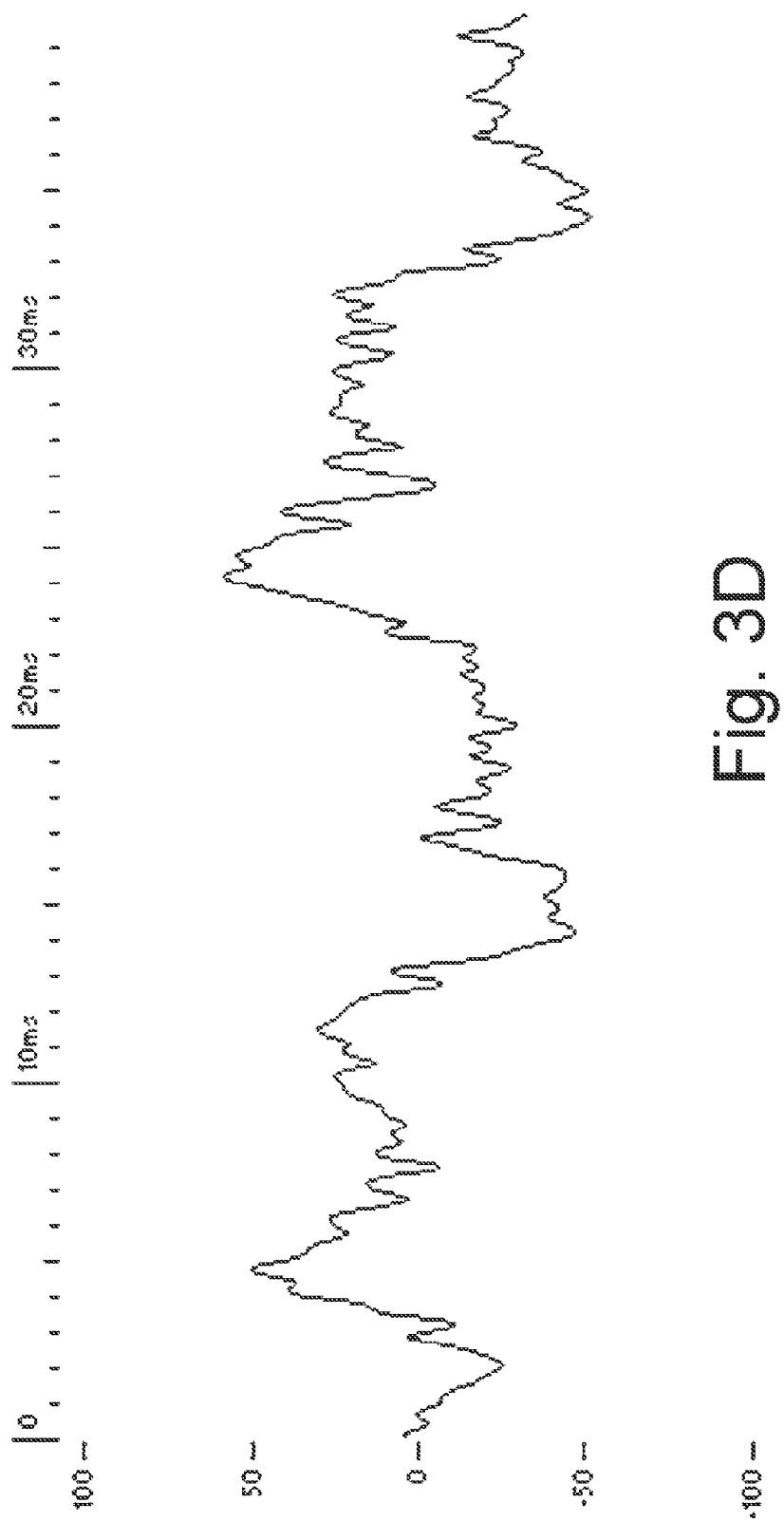
Figure 3E:
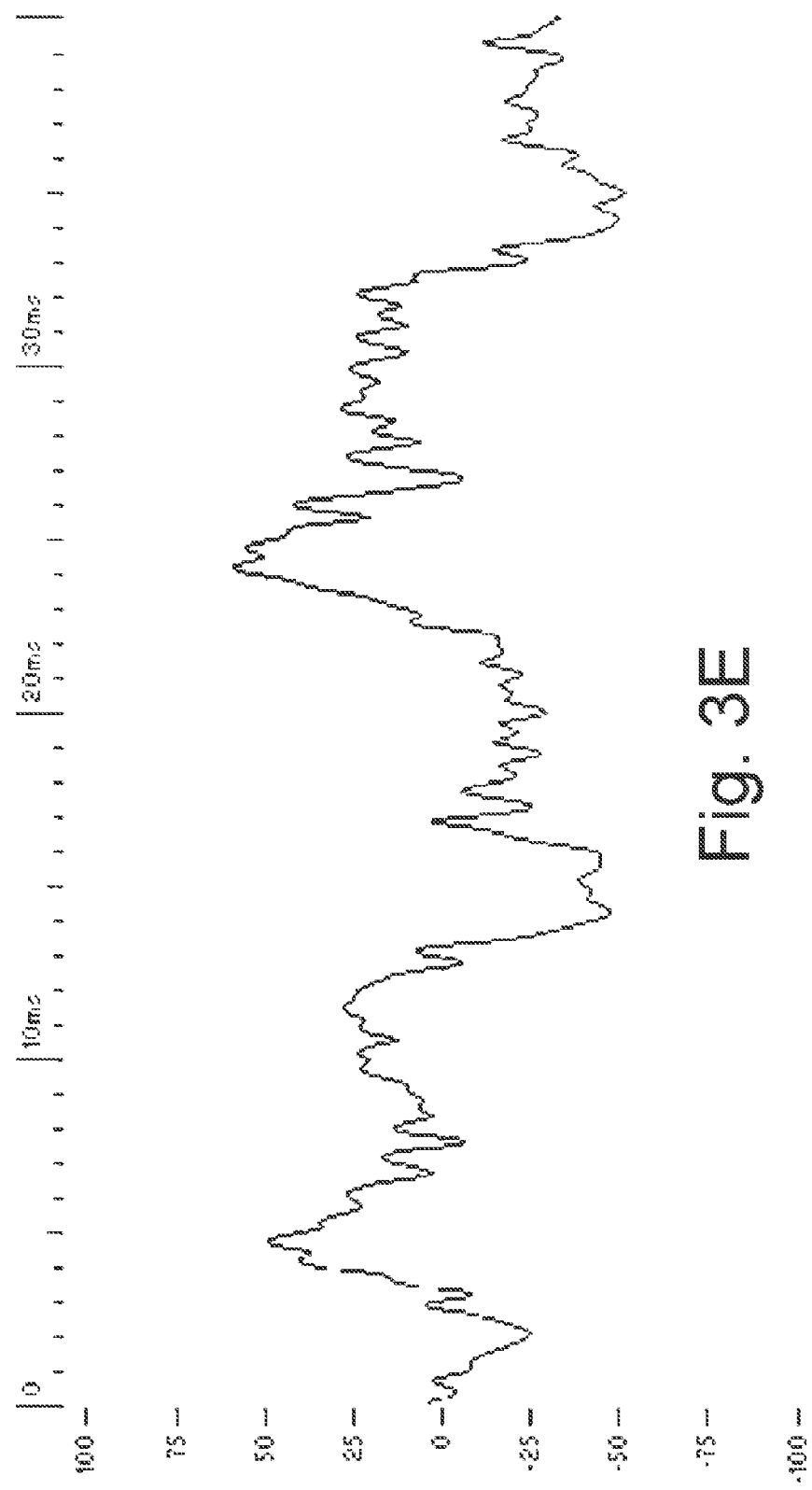
Figure 3F:
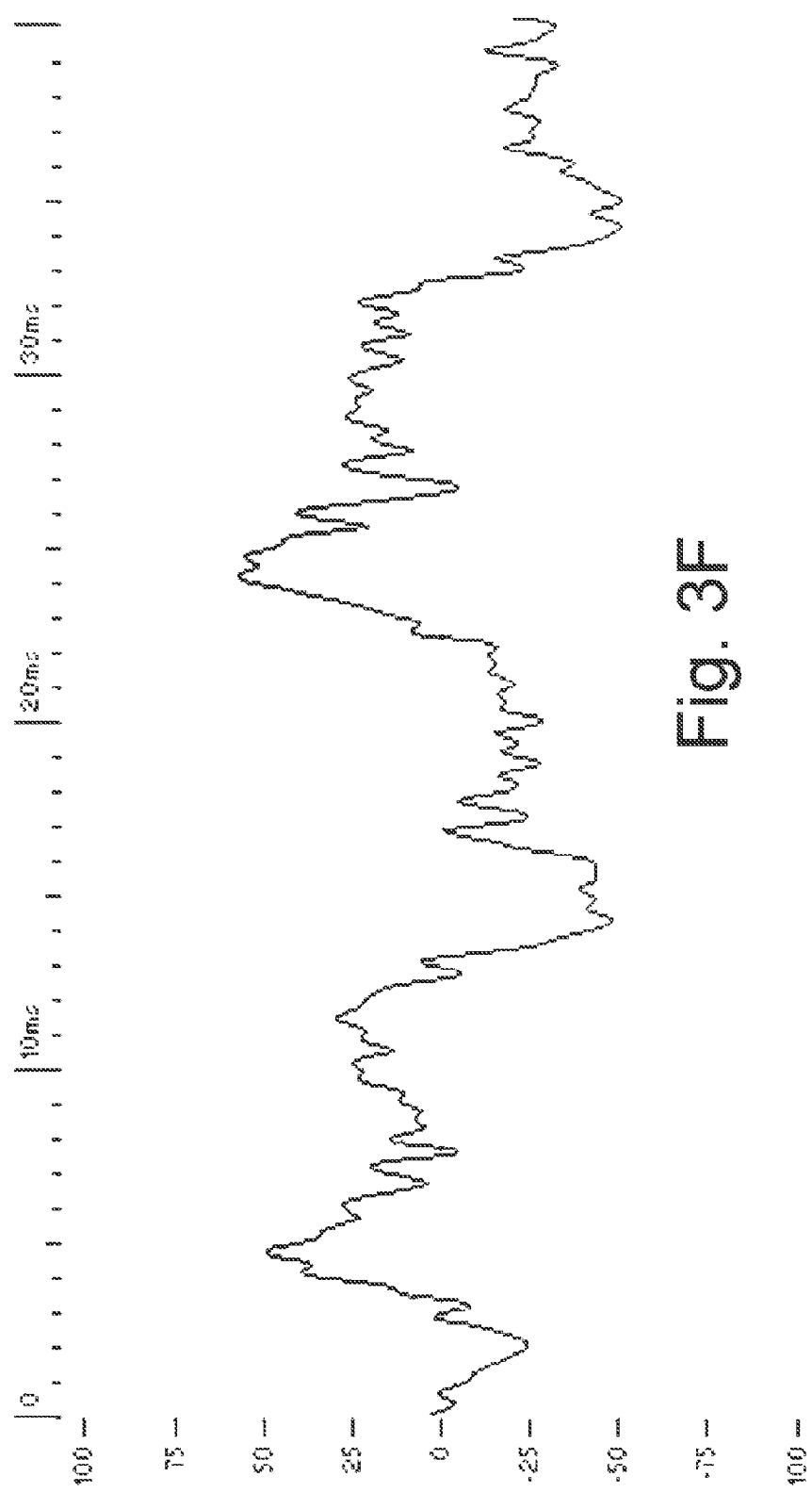
Figure 3G:
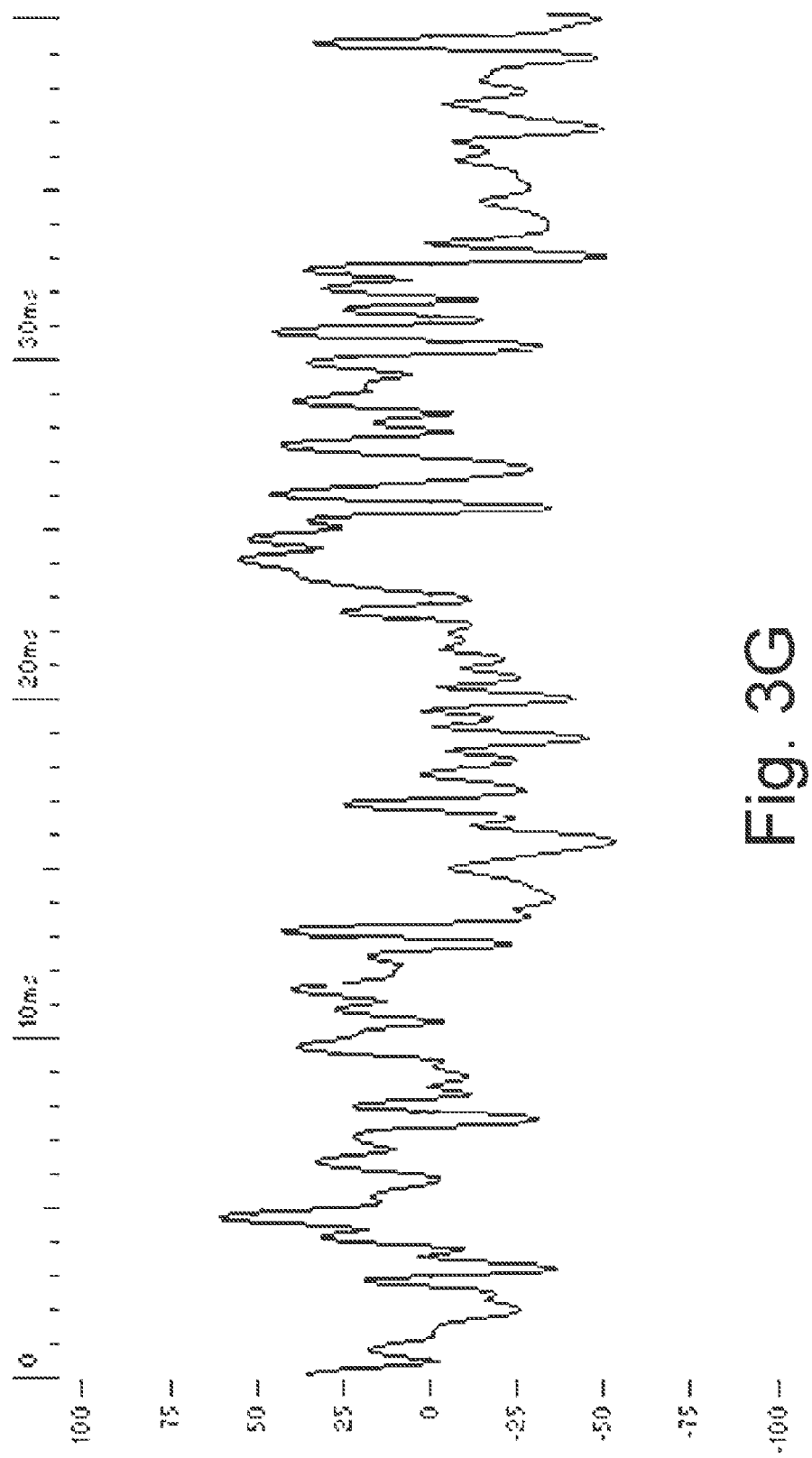
Figure 3H:
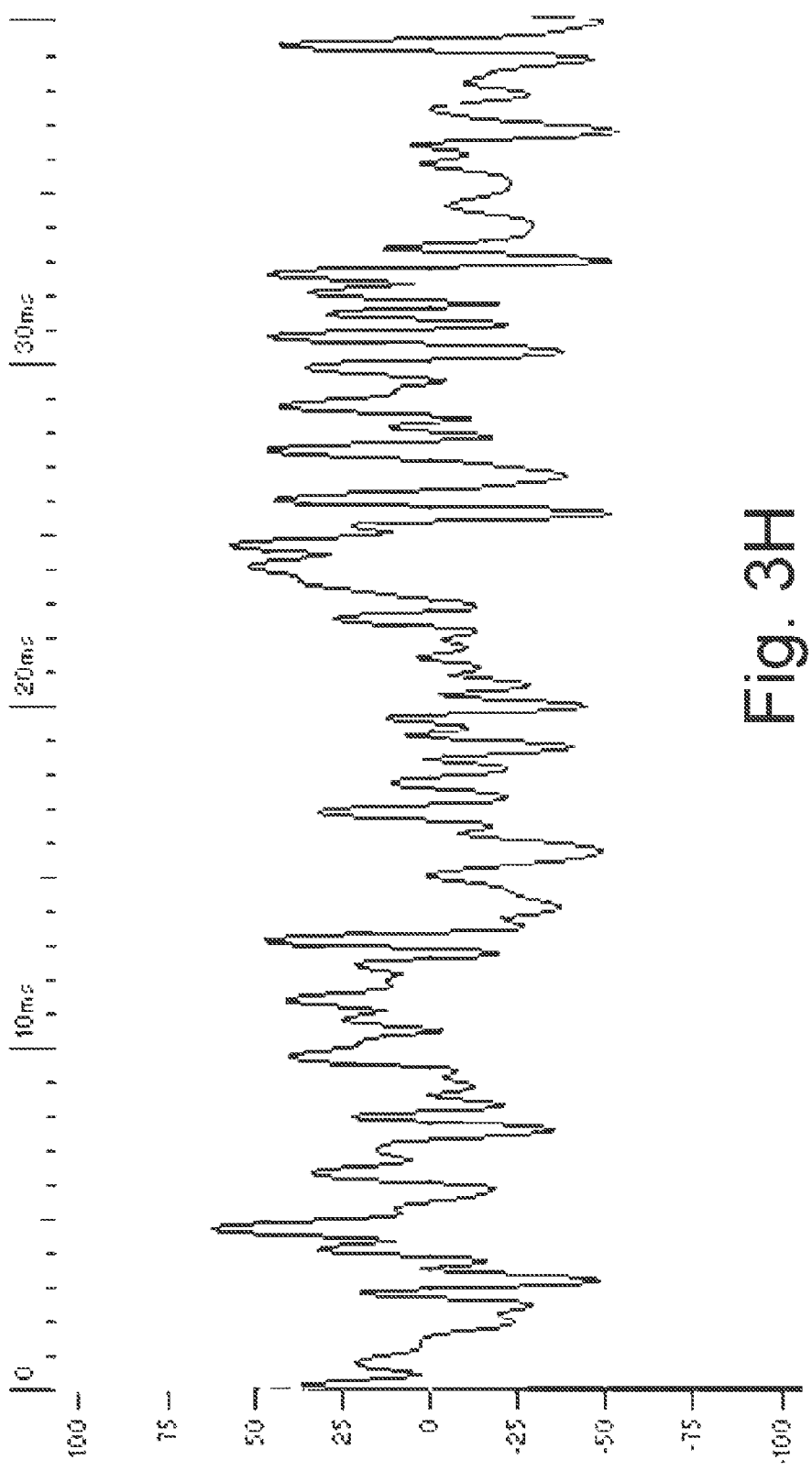
Figure 31:
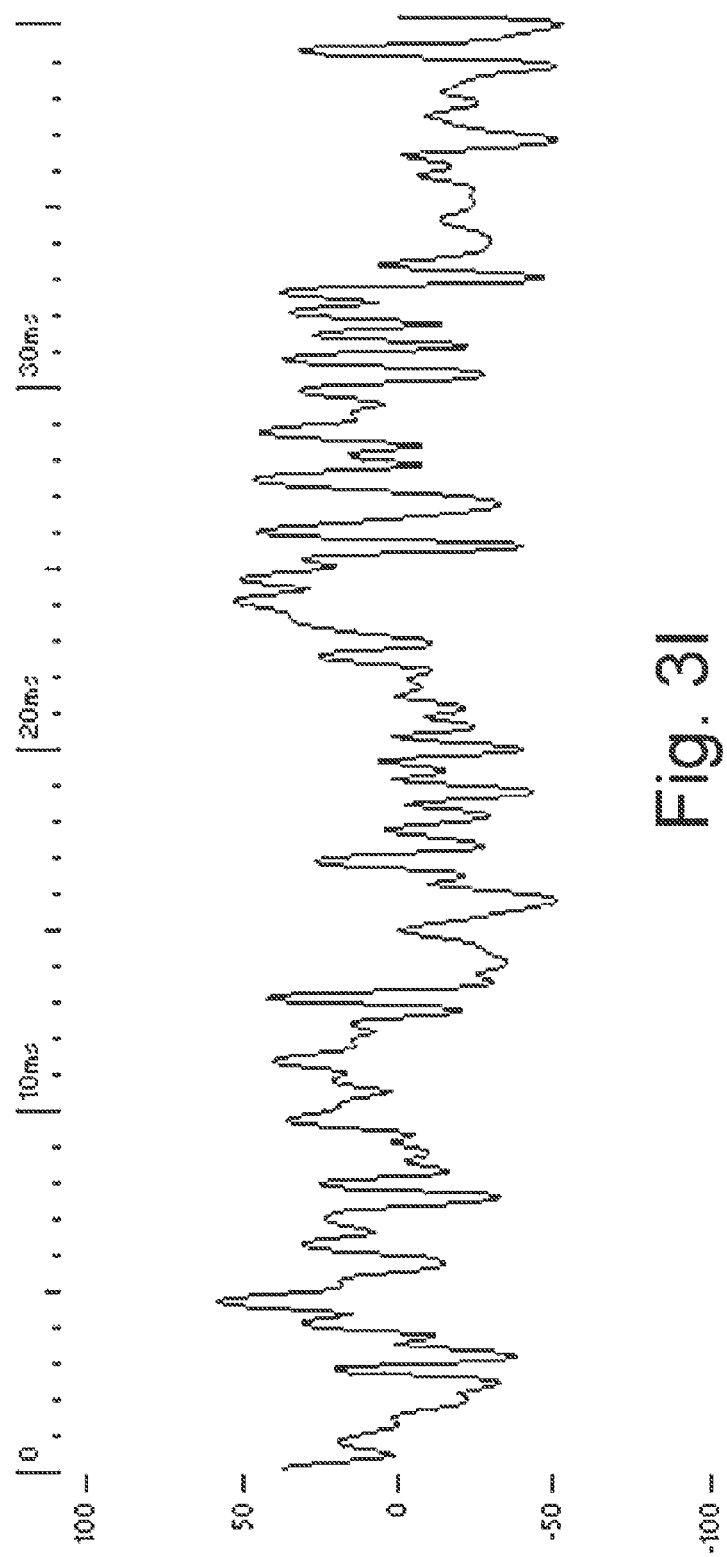
Figure 3K:
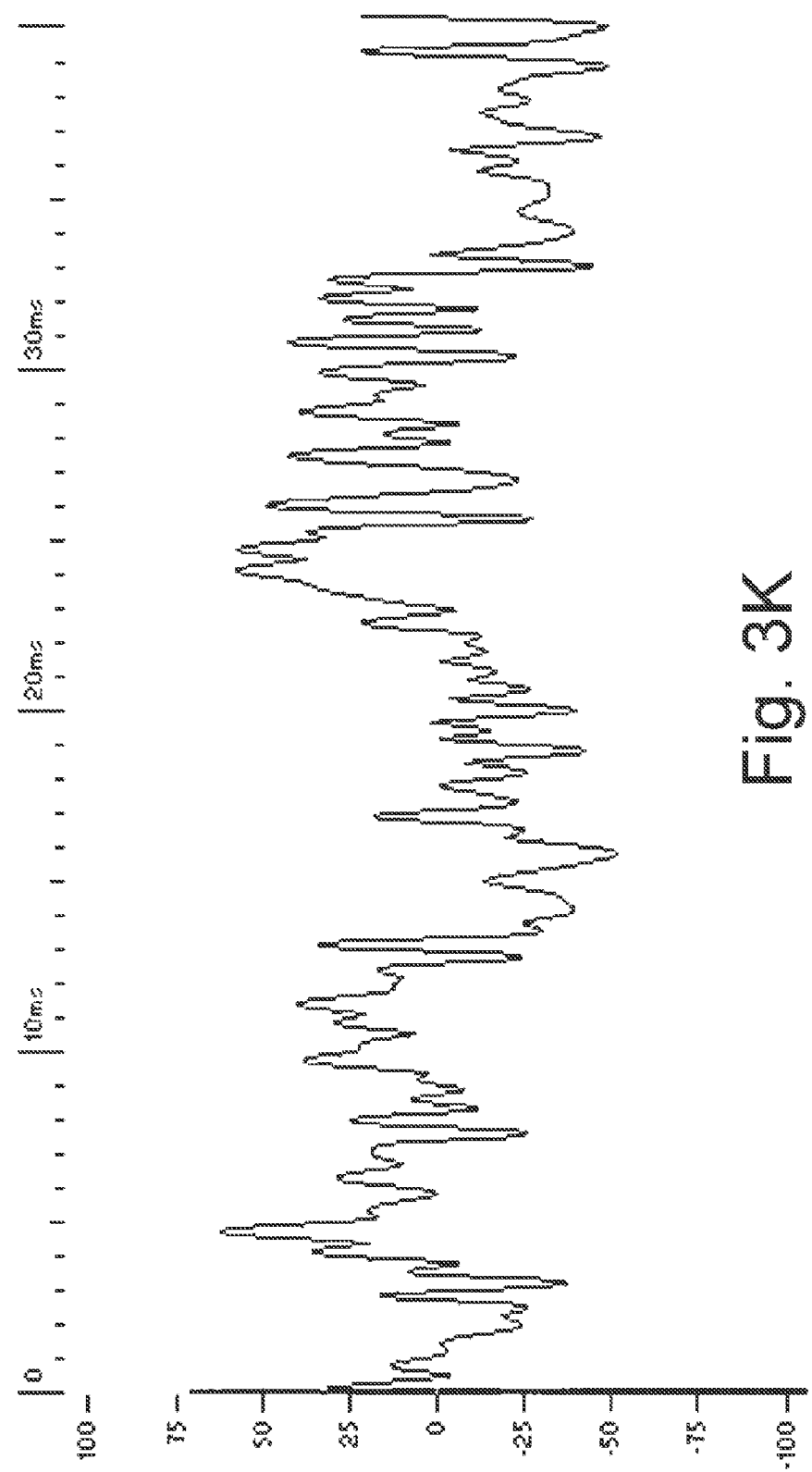
Figure 3L:
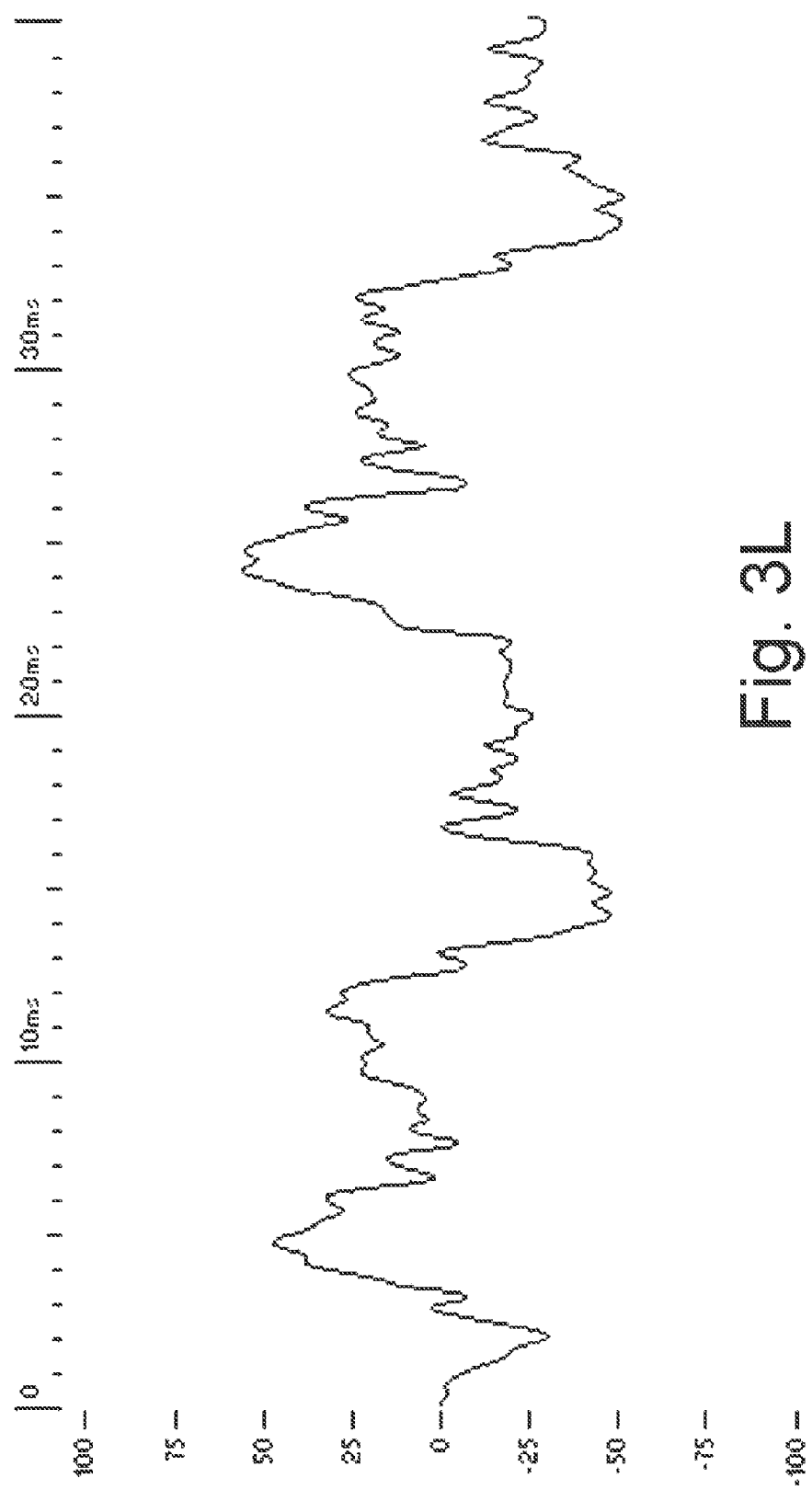
Figure 3M:
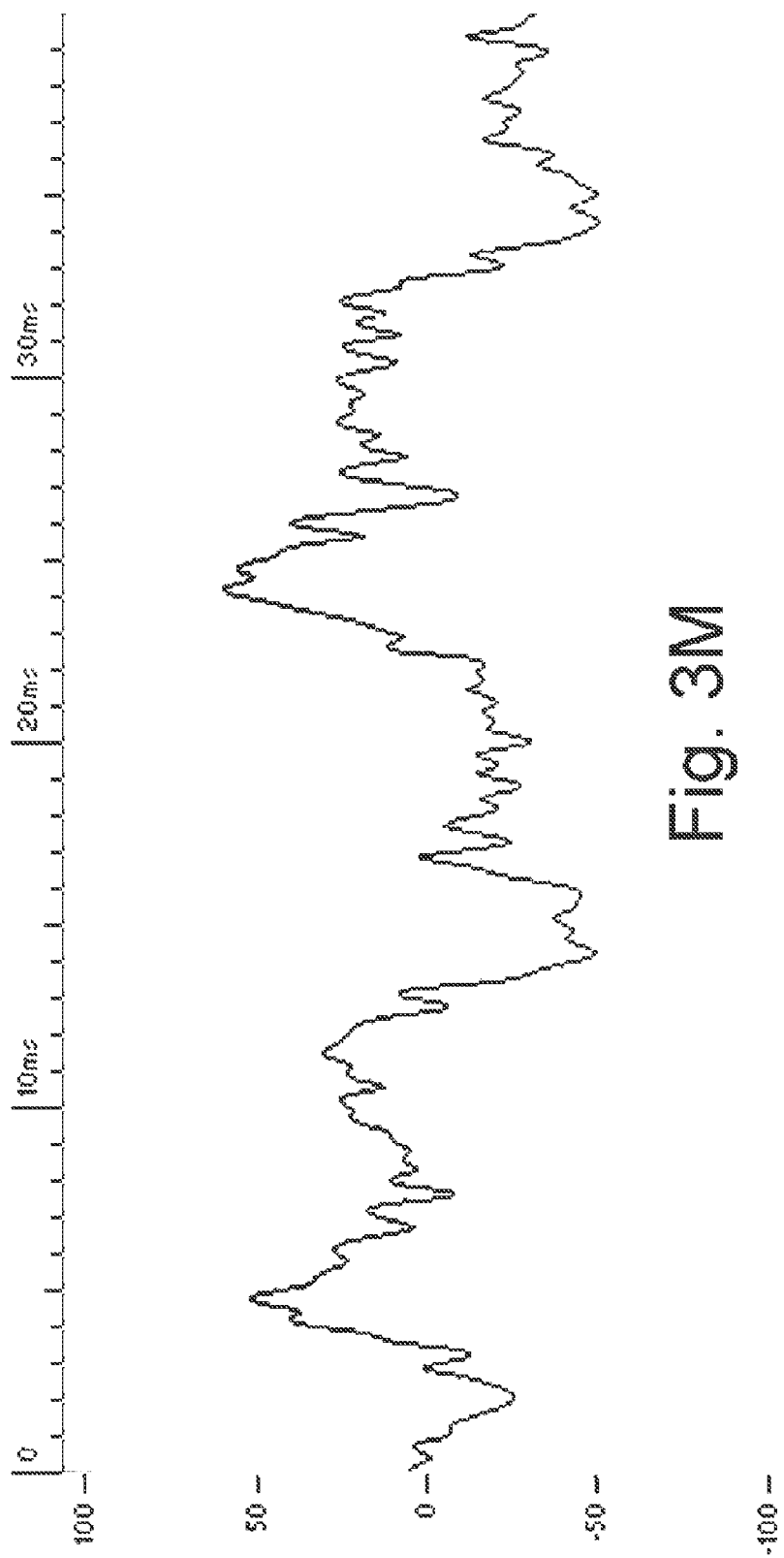
Figure 3N:
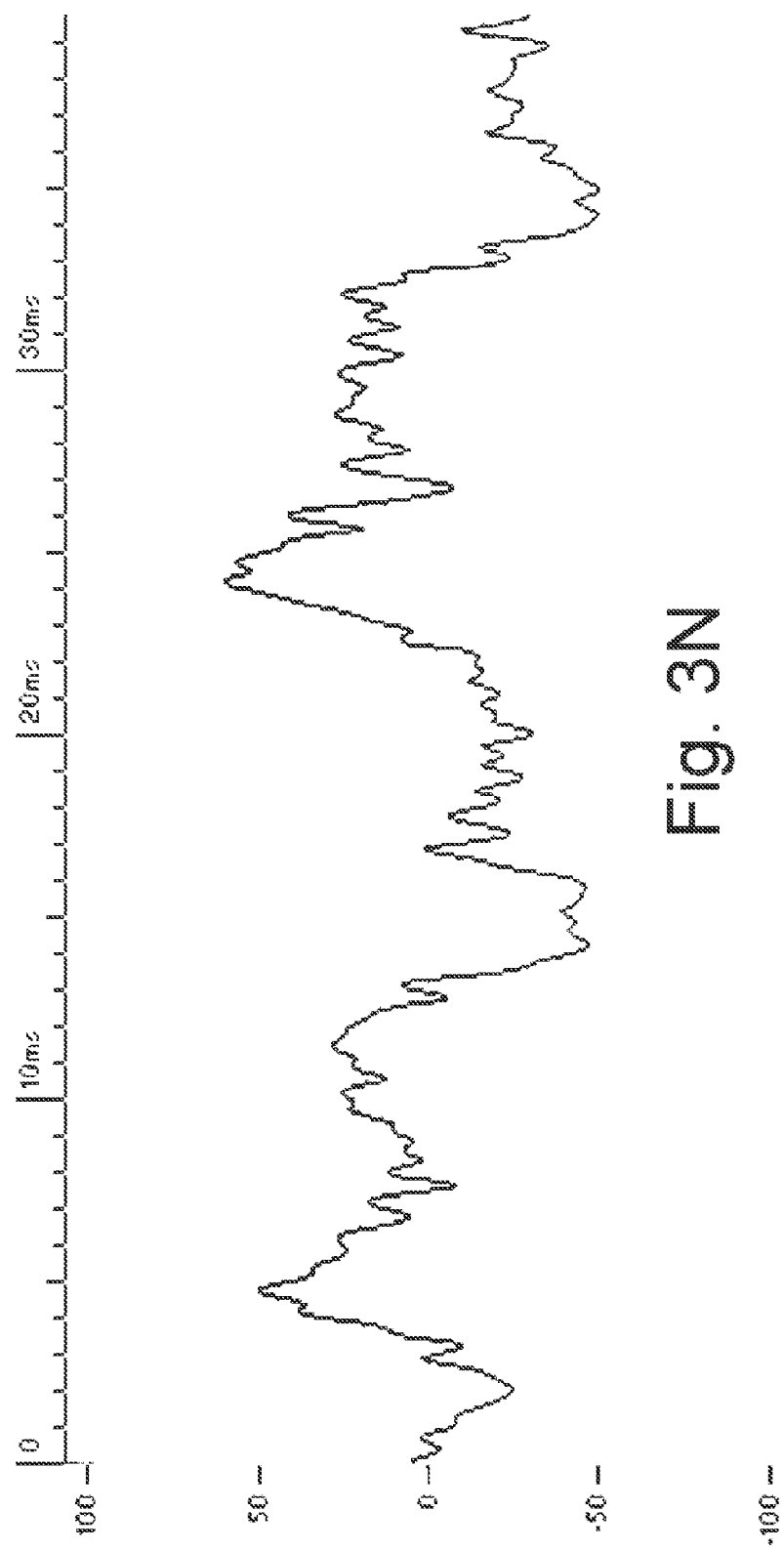
Figure 30:
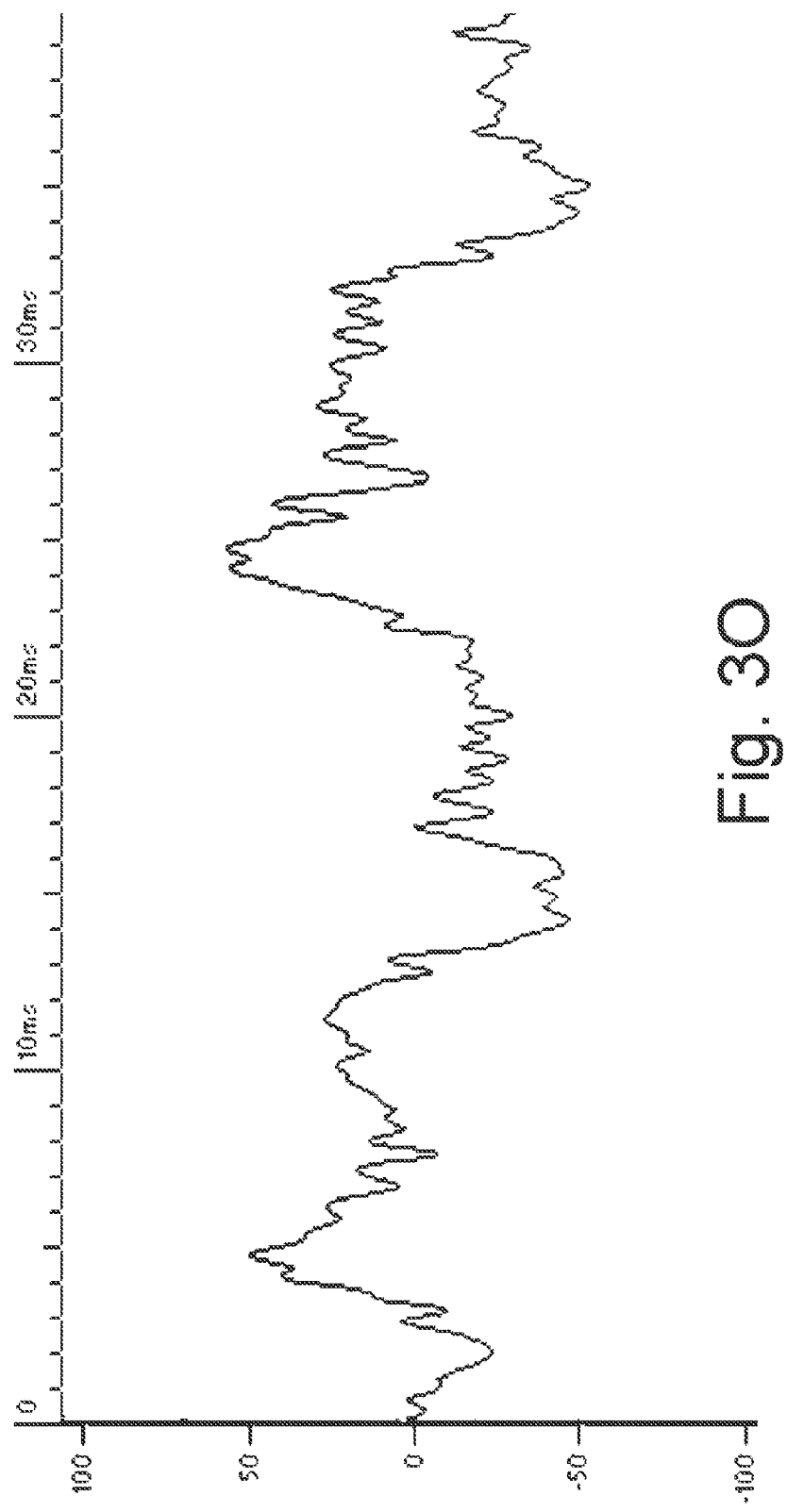

Positive dilutions were all in the range of $10^{-7}$ to $10^{-13}$ and the signal frequency profiles were similar, although small differences may exist between species and may be revealed by a more refined signal analysis. By contrast, no signals were detected from certain strains of *E. Coli* used as plasmid vector for molecular cloning such as *E. coli* XL1 B (Stratagene) and *E. coli* TOP10 (Invitrogen) and also in bacteria known to be apathogenic, such as *Lactobacillus* and *Bacillus* Calmette-Guerin. This indicated that only some specific sequences of bacterial DNA were at the origin of EMS. As shown in FIGS. 2A-2O, the EMS are recorded over 6 seconds. The data is then subject to a frequency domain transform such as a Fast Fourier Transform (FFT) as shown in FIGS. 4A-4O. The samples represent serial decimal dilution concentrations from $10^{-2}$ to $10^{-15}$ of a solution (filtered through a 100 nm pore size filter, except FIG. 2O, which was unfiltered). FIGS. 2A, 2B, 2C, 2D, 2E, 2F, 2L, 2M, 2N, and 2O are control samples (containing no DNA), showing a noise pattern, and FIGS. 2G, 2H, 2I, 2J, 2K, are dilutions of a filtered solution of DNA extracted from *E. Coli* K1. As can be seen, as compared to the control samples, the spectral energy of the EMS from the experimental samples of FIGS. 4G-4K, at frequencies greater than about 75 Hz up to about 2,000 Hz is clearly higher than the control samples. This distinction is even clearer at frequencies above 500 Hz. In the time domain plots of FIGS. 2A-2O and the zoom detail of FIGS. 3A-3O, it is visually apparent that FIGS. 2G, 2H, 2I, 2J and 2K and FIGS. 3G, 3H, 3I, 3J and 3K have higher amplitudes of high frequency signal components than the control samples.

This data suggests that a simplified analysis of spectral energy at about 1,500 Hz or more generally in the 1,400-2,000 Hz band may be sufficient to determine the presence of the effect, and therefore than a relatively simple instrument, without requiring complex analytical software, may be used for screening samples.

In an attempt to analyze the nature of the sequences involved, *Mycoplasma pirum* species was used, in which a gene indispensable for its eventual pathogenic role was cloned, the gene coding for the adhesin protein, a protein necessary for the attachment of the bacterium to eukaryotic cells.

This gene was cloned in a plasmid carried by an *E. Coli* strain in two fragments corresponding respectively to the N-terminus and the C-terminus of the protein.

The vector *E. Coli* strain (XL1 B) lacking the plasmid did not produce EMS as well as its extracted DNA.

By contrast, when the bacterial strain was transformed by the plasmids carrying the adhesin gene fragments, its extracted DNA produced EMS as well as the purified plasmid DNA.

The two gene fragments were excised by appropriate restriction enzymes from the plasmid and purified by electrophoresis in agarose gel. The electrophoretic bands corresponding to their molecular weight (respectively 1.5 Kb for the N-terminus and 3.5 Kb for C-terminus) were cut from the gel and the DNA fragments were eluted.

Again, upon the procedure previously described (filtration with 0.45 μm and 0.1 μm filters) the two pure DNA fragments corresponding to the adhesin gene each yielded typical EMS.

This result indicates that the present method is able to distinguish in a given bacterium between the specific DNA sequences which are responsible for emitting the electromagnetic signals.

The adhesin gene of *M. pirum* is, in its native state, part of the chromosomal DNA, indicating that whatever be its location, plasmidic or integrated, its sequences by themselves are able to induce EMS.

This procedure opens the way to a more refined intragenic analysis of the minimal sequences of a gene which are responsible for the EMS.

It is noted that, while the signals themselves may be similar for various DNA samples which are associated with the EMS, the DNA sequences themselves are different. Therefore, the DNA sequence giving rise to a signal may be inferred based on similarities of the EMS to the corresponding EMS of authentic samples (either gathered contemporaneously or retrieved from a database), and/or by studies which target particular DNA sequences, and thereby modify signals associated with those sequences. For example, the EMS associated with DNA may be modified by small molecule agents, binding proteins and factors, DNA (e.g., primer-type sequences) or RNA (e.g., siRNA) or other nucleic acid targeting molecules, restriction endonucleases, antibodies and immunoglobulin-type agents, etc. Therefore, even if an EMS is not itself diagnostic for a pathological condition, the selective extinction or enhancement of the EMS based on selective modification of the sample may indeed play a role in the diagnosis.

However it is already applicable for the detection of infections by pathogenic bacteria in human and animal diseases, especially when there are no available molecular or serological methods of detection.

Patients suffering from chronic diseases such as rheumatoid arthritis, multiple sclerosis, Alzheimer's and Parkinson's diseases are generally positive for EMS in their plasma. However, freezing of the plasma will abolish the emission of EMS.

Therefore, the plasma has to be analyzed soon after separation from the drawn blood.

The present method described here is a significant improvement in that it allows detection of EMS from DNA extracted from plasma stored frozen.

What is claimed is:

1. A method of analyzing electromagnetic emissions associated with deoxyribonucleic acid in an aqueous sample, comprising:
   extracting a deoxyribonucleic acid from the aqueous sample;
   filtering the extracted deoxyribonucleic acid through a filter having a pore size of less than 0.45 micron to produce a filtrate;
   diluting the filtrate comprising the filtered extracted deoxyribonucleic acid in water by at least 10 fold;
   receiving electromagnetic signals emitted by the diluted filtrate comprising a frequency band comprising about 1400 Hz to about 2000 Hz through an antenna; and
   analyzing the received electromagnetic signals received through the antenna with at least one automated processor to determine at least one characteristic of the deoxyribonucleic acid, based on at least spectral characteristics of the electromagnetic signals responsive to characteristics of the filtered extracted deoxyribonucleic acid, wherein a temperature of the diluted filtered extracted deoxyribonucleic acid remains above 0° C. and below 100° C. between said filtering and said receiving.

2. The method according to claim 1, further comprising purifying the extracted deoxyribonucleic acid in the aqueous sample prior to filtering by separating proteins.

3. The method according to claim 1, further comprising:
   preparing a control sample by heating the filtrate to at least 100° C. and treating the heated filtrate with DNAse; and
   analyzing the electromagnetic signals from the control sample.

4. The method according to claim 1, further comprising:
   preparing a control sample by freezing the filtrate,
   further comprising analyzing the electromagnetic signals from the control sample.

5. The method according to claim 1, wherein the characteristic of the deoxyribonucleic acid comprises an organism of origin of the deoxyribonucleic acid.

6. The method according to claim 1, wherein the characteristic of the deoxyribonucleic acid comprises a pathogenicity of an organism of origin of the deoxyribonucleic acid.

7. The method according to claim 1, further comprising obtaining the deoxyribonucleic acid from an animal suffering from an infection, wherein the determined at least one characteristic is selectively dependent on an infectious organism associated with the infection.

8. The method according to claim 1, further comprising extracting the deoxyribonucleic acid from at least one of blood, feces, urine, saliva, tears, seminal fluid, sweat, seminal and vaginal fluids of a human patient.

9. The method according to claim 1, wherein the filtrate is diluted by a plurality of different dilution factors prior to receiving of the electromagnetic signals, and the analyzing comprises analyzing a plurality of electromagnetic spectra associated with respective ones of the plurality of different dilution factors.

10. The method according to claim 1, wherein said analyzing comprises comparing spectral characteristics of the electromagnetic signals with a corresponding electromagnetic signals derived from a deoxyribonucleic acid from a different source.

11. The method according to claim 1, wherein said analyzing comprises determining a change in characteristics over time of the electromagnetic signals.

12. The method according to claim 1, wherein said analyzing comprises:
   determining a background noise of the received electromagnetic signals over a range of frequencies from a sample which has a substantial absence of deoxyribonucleic acid-associated electromagnetic signals, and
   applying an adaptive threshold to detect significant electromagnetic signals above the background noise from the sample containing the deoxyribonucleic acid.

13. The method according to claim 12, wherein said analyzing comprises determining a change over time of signal energy as a function of frequency over a frequency range of about 500 Hz to 3,000 Hz.

14. The method according to claim 1, wherein the filtrate comprises deoxyribonucleic acid diluted in water to a concentration of about $10^{-7}$.

15. The method according to claim 1, wherein the filtering comprises filtering the deoxyribonucleic acid through a filter having a pore size of about 0.1 μm.

16. A method of analyzing electromagnetic emissions associated with deoxyribonucleic acid, comprising:
- extracting deoxyribonucleic acid from a biological specimen;
- filtering the deoxyribonucleic acid in an aqueous solution through a filter having a pore size of less than about 0.45 micron to produce a filtrate;
- diluting the filtrate comprising the filtered extracted deoxyribonucleic acid in water by at least 100 fold;
- permitting environmental electromagnetic background to excite resonances in the diluted filtered extracted deoxyribonucleic acid;
- receiving electromagnetic signals emitted by the diluted filtrate comprising a frequency in a band comprising about 1400 Hz to about 2000 Hz from an antenna; and
- analyzing the received electromagnetic signals with at least one automated processor to determine at least one characteristic of the deoxyribonucleic acid, based on at least spectral characteristics of the received electromagnetic signals, at least one negative control known to produce no electromagnetic emissions associated with deoxyribonucleic acid and at least one positive control known to produce electromagnetic emissions associated with deoxyribonucleic acid.

17. The method according to claim 16,
- wherein the at least one negative control comprises at least one of:
- a first control sample prepared by heating the filtrate to at least 100° C. and treating the heated filtrate with DNAse; and
- a second control sample prepared by freezing the filtrate; and
- wherein the at least one positive control comprises diluted filtered extracted deoxyribonucleic acid from a known source, which has been maintained under conditions which preserve electromagnetic signal emission.

18. A system for analyzing electromagnetic emissions associated with deoxyribonucleic acid, comprising:
- a proteinase, configured to degrade proteins associated with the deoxyribonucleic acid;
- a precipitation solution, configured to precipitate the deoxyribonucleic acid after degradation of the proteins associated with the deoxyribonucleic acid;
- an aqueous solution for resuspending the precipitated deoxyribonucleic acid;
- a filter having a pore size of less than about 0.45 micron configured to filter the deoxyribonucleic acid resuspended in the aqueous solution, to produce a filtrate;
- a supply of water, configured to dilute the filtrate comprising the filtered ressupended deoxyribonucleic acid in water by at least 10 fold;
- an antenna configured to receive electromagnetic signals emitted by the diluted filtrate comprising a frequency in a band comprising at least about 1400 Hz to about 2000 Hz; and
- at least one automated processor configured to determine at least one characteristic of the deoxyribonucleic acid sensitive to at least one of a temperature above 100° C. and a temperature below 0° C., based on at least spectral characteristics of the received electromagnetic signals.

19. The system according to claim 18, wherein the antenna is configured to receive electromagnetic signals emitted by the diluted filtrate comprising the frequency band comprising about 20 Hz to about 20,000 Hz.

20. The system according to claim 18, further comprising:
- an amplifier, configured to amplify the received electromagnetic signals emitted by the diluted filtrate; and
- an output port configured to communicate data dependent on the determined characteristic;
- wherein the at least one automated processor is further configured to determine a background noise over a range of frequencies in the amplified signals from a sample which has a substantial absence of emitted deoxyribonucleic acid-associated electromagnetic signals, and to apply an adaptive threshold to detect significant electromagnetic field components over a range of frequencies above the adaptive threshold from the diluted filtrate containing the deoxyribonucleic acid.

* * * * *